US012636071B2

(12) United States Patent
Privitera et al.

(10) Patent No.: US 12,636,071 B2
(45) Date of Patent: May 26, 2026

(54) SURGICAL CLAMP

(71) Applicant: AtriCure, Inc., Mason, OH (US)

(72) Inventors: Salvatore Privitera, Mason, OH (US);
Kenneth Lance Miller, Hamilton, OH
(US); Melissa Deitzer, Cincinnati, OH
(US); Douglas J. Seith, Tampa, FL
(US); Akiva Kirschner, Cincinnati, OH
(US); Sydney Gaynor, Cincinnati, OH
(US); Kurtis Klingenberg, Cincinnati,
OH (US)

(73) Assignee: AtriCure, Inc., Mason, OH (US)

( * ) Notice: Subject to any disclaimer, the term of this
patent is extended or adjusted under 35
U.S.C. 154(b) by 110 days.

(21) Appl. No.: 18/311,298

(22) Filed: May 3, 2023

(65) Prior Publication Data

US 2023/0355297 A1     Nov. 9, 2023

Related U.S. Application Data

(63) Continuation of application No. 16/736,694, filed on
Jan. 7, 2020, now Pat. No. 11,678,928.

(60) Provisional application No. 62/947,573, filed on Dec.
13, 2019, provisional application No. 62/874,150,
filed on Jul. 15, 2019, provisional application No.
62/796,998, filed on Jan. 25, 2019, provisional
application No. 62/790,938, filed on Jan. 10, 2019.

(51) Int. Cl.
*A61B 18/14* (2006.01)
*A61B 18/00* (2006.01)
(52) U.S. Cl.
CPC .................... *A61B 18/1445* (2013.01); *A61B
2018/00351* (2013.01); *A61B 2018/00577*
(2013.01)

(58) Field of Classification Search
CPC .................. A61B 2018/00577; A61B 18/1445
See application file for complete search history.

(56) References Cited

U.S. PATENT DOCUMENTS

| | | | | |
|---|---|---|---|---|
| 5,618,307 A | * | 4/1997 | Donlon | ................... A61B 17/29 |
| | | | | 606/208 |
| 7,288,092 B2 | * | 10/2007 | Hooven | ............. A61B 18/1445 |
| | | | | 606/51 |
| 10,136,909 B2 | * | 11/2018 | Ibrahim | ................. A61B 17/29 |

(Continued)

*Primary Examiner* — Linda C Dvorak
*Assistant Examiner* — Ryan T Clark
(74) *Attorney, Agent, or Firm* — Dorton & Willis LLP;
Ryan Willis

(57)     ABSTRACT

Surgical devices and related methods are disclosed. An
example surgical device may include an end effector dis-
posed at a distal end of the shaft, the end effector comprising
a head, the head comprising an articulating mechanism, the
articulating mechanism being operable to move a first jaw
between an open position in which the first jaw and a second
jaw are separated and substantially non-parallel and a closed
position in which the first jaw and the second jaw are
substantially adjacent and substantially parallel, where each
of the first jaw and the second jaw comprises a first sub-
stantially straight portion proximate the head, a second
substantially straight portion, a third substantially straight
portion distant from the head, a first curved portion between
the first substantially straight portion and the second sub-
stantially straight portion, and a second curved portion
between the second substantially straight portion and the
third substantially straight portion.

16 Claims, 14 Drawing Sheets

(56) References Cited

U.S. PATENT DOCUMENTS

| | | | |
|---|---|---|---|
| 2003/0073991 A1* | 4/2003 | Francischelli | ..... A61B 18/1445 |
| | | | 606/41 |
| 2006/0271042 A1* | 11/2006 | Latterell | ............ A61B 18/1445 |
| | | | 606/51 |
| 2016/0015448 A1* | 1/2016 | Longoria | ............... A61B 90/03 |
| | | | 606/41 |

* cited by examiner

700

702

706 516 504

514 502

704

708

704

722 720 718

724 714 712 716

820             816

814             806

822        816       824

826

814             806

828      816    830

SURGICAL CLAMP

CROSS REFERENCE TO RELATED APPLICATIONS

This application is a continuation of U.S. Nonprovisional application Ser. No. 16/736,694, filed Jan. 7, 2020, which claims the benefit of U.S. Provisional Application No. 62/790,938, filed Jan. 10, 2019, U.S. Provisional Application No. 62/796,998, filed Jan. 25, 2019, U.S. Provisional Application No. 62/874,150, filed Jul. 15, 2019, and U.S. Provisional Application No. 62/947,573, filed Dec. 13, 2019, which are incorporated by reference.

INTRODUCTION TO THE INVENTION

The present disclosure is directed to medical instruments and devices and related methods, and, more specifically, to surgical devices for clamping and ablating tissue and related methods.

The present disclosure contemplates that atrial fibrillation is a common heart arrhythmia, affecting millions of people in the United States alone. Ablation of cardiac tissue, in order to create scar tissue that poses an interruption in the path of the errant electrical impulses in the heart tissue, is a commonly performed procedure to treat cardiac arrhythmias. Ablation has been achieved or suggested using a variety of techniques, such as freezing via cryogenic probe, heating via radio frequency (RF) energy, surgical cutting, and other techniques. As used here, "ablation" may refer to the removal or destruction of the function of a body part, such as cardiac tissue, regardless of the apparatus or process used to carry out the ablation. Also, as used herein, "transmural" may refer to through the wall or thickness, such as through the wall or thickness of a hollow organ or vessel. Generally, ablation of cardiac tissue may be carried out in an open surgical procedure, where the breastbone is divided and the surgeon has direct access to the heart, or through a minimally invasive route, such as between the ribs or via catheter that is introduced through a vein, and into the heart.

The present disclosure contemplates that although clamp-type ablation devices have been designed for use concomitant to coronary artery bypass graft procedures, only a small percentage of patients with atrial fibrillation undergoing coronary artery bypass graft procedures are being treated for atrial fibrillation.

The present disclosure contemplates that problems encountered in cardiac ablation procedures may include difficulty in precisely locating the target tissue and difficulties related to the ablation of the tissue. For example, in some circumstances, it may be difficult to position an ablation device at a specific, desired location on the heart due to the structure of the heart. As an example, some ablation procedures involve isolating the pulmonary veins. Because the pulmonary veins are on the posterior side of the heart, it may be difficult to position an ablation device to achieve the desired ablations. As another example, in some circumstances, it may be difficult to create a continuous, sufficiently deep (e.g., transmural) line of ablated tissue, which may be necessary to electrically isolate a portion of the heart. This difficulty may be particularly relevant when an ablation procedure involves sequentially creating a series of shorter lesions at different positions that, together, are intended to form a continues lesion.

While known devices have been used safely and effectively to clamp and ablate tissue (such as cardiac tissue), improvements in the construction and operation of surgical devices for clamping and ablating tissue may be beneficial for users (e.g., surgeons) and patients. The present disclosure includes various improvements which may enhance the construction, operation, and methods of use of surgical devices for clamping and ablating tissue, such as cardiac tissue.

It is a first aspect of the present disclosure to provide an end effector for a surgical device including a first jaw; a second jaw; and an articulating mechanism operable to move the first jaw between an open position in which the first jaw and the second jaw are separated and substantially non-parallel, an intermediate position in which the first jaw and the second jaw are separated and substantially parallel, and a closed position in which the first jaw and the second jaw are substantially adjacent and substantially parallel. The articulating mechanism may include a first jaw mount coupled to the first jaw, the first jaw mount being movable along a path, wherein movement of the first jaw mount along the path causes rotation and translation of the first jaw mount and the first jaw, thereby moving the first jaw between the open position, the intermediate position, and the closed position; and a pivotably mounted crank, the crank operably coupling an actuator linkage to the first jaw mount so that moving the actuator linkage rotates the crank, wherein rotation of the crank moves the first jaw mount along the path.

In a more detailed embodiment of the first aspect, the path may include at least one straight portion and at least one curved portion. The path may be at least partially defined by a slot. A first pin may be movably disposed in the slot for movement along the path. The first jaw mount may include the first pin. Movement of the first jaw mount along the path may include movement of the first pin along the slot. The first jaw mount may include a second pin movably disposed in the slot for movement along the path.

In a more detailed embodiment of the first aspect, the end effector may include a connecting linkage having a proximal end and a distal end, the connecting linkage operatively interposing the actuator linkage and the crank. The proximal end of the connecting linkage may be pivotably coupled to the actuator linkage and/or the distal end of the connecting linkage may be pivotably coupled to the crank. The proximal end of the connecting linkage may include a guide slidably disposed in a guide slot. The guide slot may be generally linear and/or may be oriented generally in-line with the actuator linkage.

In a more detailed embodiment of the first aspect, the crank may include a first arm and a second arm. The first arm of the crank may be operatively coupled to the actuator linkage and/or the second arm of the crank may be slidably and/or pivotably coupled to the first jaw mount. The second arm of the crank may include a crank slot and/or the first jaw mount may include a pin. The pin may move along the crank slot as the crank rotates and the first jaw mount moves along the path. The crank slot may be substantially straight and/or the crank slot may be oriented substantially radially with respect to an axis of rotation of the crank.

In a more detailed embodiment of the first aspect, each of the first jaw and the second jaw may include a first end portion proximate the articulating mechanism and a second end portion generally away from the articulating mechanism, each second end portion terminating at a respective tip.

In a more detailed embodiment of the first aspect, a surgical device may include a shaft; an end effector as described above disposed at a distal end of the shaft; and a handle disposed at a proximal end of the shaft. The handle may include an actuator operatively coupled to the actuator linkage and/or the actuator linkage may extend longitudinally through the shaft to the end effector. The end effector may include a head at least partially containing the articulating mechanism, the first jaw and/or the second jaw may be disposed generally distally on the head, and/or the first jaw and the second jaw may be oriented generally laterally from the head.

In a more detailed embodiment of the first aspect, in the open position, the tip of the first jaw and/or the tip of the second jaw may be spaced apart and/or at least partially define an open mouth. Each of the tip of the first jaw and/or the tip of the second jaw may be configured to releasably couple with at least one of a first end portion and/or a second end portion of a flexible guide. The tip of the first jaw may be configured to magnetically releasably couple with the first end portion of the flexible guide and/or the tip of the second jaw may be configured to magnetically releasably couple with the second end portion of the flexible guide.

In a more detailed embodiment of the first aspect, each of the first jaw and/or the second jaw may include a plurality of substantially straight portions interposed by curved portions. At least one of the first jaw and/or the second jaw may be configured to ablate tissue clamped therebetween. Each of the first jaw and/or the second jaw may include a pair of elongated, spaced-apart electrodes operatively coupled to a source of radio frequency energy for ablating tissue clamped between the first jaw and the second jaw. The electrodes of each pair of electrodes may be spaced apart from about 0.1 mm to about 3.0 mm.

It is a second aspect of the present disclosure to provide a surgical device including a distal handle comprising an actuator; a shaft extending distally from the handle, the shaft comprising an actuator linkage extending therethrough, the actuator linkage being operatively coupled to the actuator; and/or an end effector disposed at a distal end of the shaft. The end effector may include a head, a first jaw disposed distally on the head, second jaw disposed distally on the head, and/or an articulating mechanism. The articulating mechanism may include a connecting linkage including a proximal end and/or a distal end, the proximal end of the connecting linkage being pivotably coupled to a distal end of the actuator linkage, a pivotably mounted crank including a first arm and a second arm, the first arm being pivotably coupled to the distal end of the connecting linkage, and/or a first jaw mount rigidly affixed to the first jaw, the first jaw mount being pivotably and slidably coupled to the second arm of the crank; wherein moving the actuator on the handle is operable to move the first jaw from an open position in which the first jaw and the second jaw are separated and substantially non-parallel to a closed position in which the first jaw and the second jaw are substantially adjacent and substantially parallel.

In a more detailed embodiment of the second aspect, the first jaw mount may be movable along a path. Movement of the first jaw mount along the path may cause rotation and/or translation of the first jaw mount and the first jaw, thereby moving the first jaw from the open position to the closed position. Rotation of the crank may move the first jaw mount along the path. The first jaw and/or the second jaw may extend generally laterally with respect to the shaft. Moving the actuator on the handle may be operable to move the first jaw between the open position, an intermediate position in which the first jaw and the second jaw are separated and substantially parallel, and/or the closed position. The second arm of the crank may include a crank slot and/or the first jaw mount may include a pin. The pin may move along the crank slot as the crank rotates. The proximal end of the connecting linkage may include a guide slidably disposed in a guide slot. The guide slot may be generally linear and/or may be oriented generally in-line with the actuator linkage. The actuator may include a plunger that is depressed distally to move the first jaw from the open position to the closed position. The shaft may be substantially rigid. At least a portion of the shaft may be bendable. The shaft may be substantially straight. Each of the first jaw and/or the second jaw may terminate at a respective tip. In the open position, the tip of the first jaw and/or the tip of the second jaw may be spaced apart and/or at least partially define an open mouth. The tip of the first jaw and/or the tip of the second jaw may be configured to releasably couple to respective end portions of an elongate, flexible guide. Each of the first jaw and/or the second jaw may include a plurality of substantially straight portions interposed by curved portions. Each of the first jaw and/or the second jaw may include at least one electrode operatively coupled to a source of radio frequency energy for ablating tissue clamped between the first jaw and/or the second jaw.

It is a third aspect of the present disclosure to provide a surgical device including a shaft and/or an end effector disposed at a distal end of the shaft, the end effector including a head, the head including an articulating mechanism, the articulating mechanism being operable to move a first jaw between an open position in which the first jaw and a second jaw are separated and substantially non-parallel and a closed position in which the first jaw and the second jaw are substantially adjacent and substantially parallel. Each of the first jaw and/or the second jaw may include a first substantially straight portion proximate the head, a second substantially straight portion, a third substantially straight portion distant from the head, a first curved portion between the first substantially straight portion and the second substantially straight portion, and/or a second curved portion between the second substantially straight portion and the third substantially straight portion. Each of the first jaw and/or the second jaw may terminate at a respective tip proximate the third substantially straight portion. In the open position, the tip of the first jaw and/or the tip of the second jaw may be spaced apart and/or at least partially define an open mouth.

In a more detailed embodiment of the third aspect, the articulating mechanism may be operable to rotate and/or translate the first jaw between the open position, an intermediate position in which the first jaw and the second jaw are separated and/or substantially parallel, and/or the closed position. The first substantially straight portion, the second substantially straight portion, and/or the third substantially straight portion of the first jaw may be obliquely oriented with respect to each other. The first substantially straight portion, the second substantially straight portion, and/or the third substantially straight portion of the second jaw may be obliquely oriented with respect to each other. The first substantially straight portion, the second substantially straight portion, and/or the third substantially straight portion of the first jaw may be substantially coplanar. The first substantially straight portion, the second substantially straight portion, and/or the third substantially straight portion of the second jaw may be substantially coplanar. The first substantially straight portion, the second substantially straight portion, and/or the third substantially straight portion of the second jaw may be substantially coplanar with the shaft.

In a more detailed embodiment of the third aspect, the second substantially straight portion of the first jaw may be longer than at least one of the first substantially straight portion of the first jaw and/or the second substantially straight portion of the first jaw. The second substantially straight portion of the first jaw may be longer than both of the first substantially straight portion of the first jaw and/or the second substantially straight portion of the first jaw.

In a more detailed embodiment of the third aspect, the first jaw and/or the second jaw may be disposed generally distally on the head. The first jaw and/or the second jaw may be oriented generally laterally from the head. In the closed position, the second substantially straight portion of the first jaw may be oriented approximately perpendicularly to the shaft.

In a more detailed embodiment of the third aspect, in the closed position, the first substantially straight portion of the first jaw may extend generally diagonally distally and/or laterally away from the head. The third substantially straight portion of the first jaw may extend generally diagonally proximally and laterally away from the second curved portion. The second jaw may be rigidly disposed with respect to the shaft. The first substantially straight portion, the second substantially straight portion, and/or the third substantially straight portion of the second jaw may be substantially coplanar with the shaft.

In a more detailed embodiment of the third aspect, the device may include a handle disposed proximally on the shaft, and the handle may include an actuator operatively connected to the articulating mechanism. The tip of the first jaw and/or the tip of the second jaw may be configured to releasably couple to respective end portions of an elongate, flexible guide. Each of the first jaw and/or the second jaw may include at least one electrode operatively coupled to a source of radio frequency energy for ablating tissue clamped between the first jaw and/or the second jaw. The articulating mechanism may include a first jaw mount coupled to the first jaw, the first jaw mount being movable along a path, wherein movement of the first jaw mount along the path causes rotation and/or translation of the first jaw mount and the first jaw, thereby moving the first jaw between the open position and the closed position; and/or a pivotably mounted crank, the crank operably coupling an actuator linkage to the first jaw mount so that moving the actuator linkage rotates the crank, wherein rotation of the crank moves the first jaw mount along the path.

It is a fourth aspect of the present disclosure to provide a guide for a surgical device, the guide including an elongate, flexible guide body including a first end portion and a second end portion; a first guide connector disposed on the first end portion; and/or a second guide connector disposed on the second end portion. The first guide connector may be selectively releasably connectable to the second guide connector and/or at least one of a first tip of a first jaw of a surgical device and/or a second tip of a second jaw of the surgical device. The second guide connector may be selectively releasably connectable to the first guide connector and/or at least one of the first tip and/or the second tip. When the first guide connector is connected to the second guide connector, the guide may form a closed loop.

In a more detailed embodiment of the fourth aspect, the first guide connector may include a first permanent magnet. The second guide connector may include a second permanent magnet. The first permanent magnet and/or the second permanent magnet may be oriented so that opposite magnetic poles face away from the guide body, thereby allowing the first guide connector and the second guide connector to magnetically couple to one another to form the guide into the closed loop. The first guide connector may include a cover configured to receive the first permanent magnet therein. The first permanent magnet may be securely contained within the cover of the first guide connector. The second guide connector may include a cover configured to receive the second permanent magnet therein. The second permanent magnet may be securely contained within the cover of the second guide connector.

In a more detailed embodiment of the fourth aspect, the guide body may be generally tubular.

In a more detailed embodiment of the fourth aspect, a surgical apparatus may include a surgical device including a handle, a shaft extending distally from the handle, and/or an end effector disposed proximate a distal end of the shaft, the end effector comprising the first jaw and the second jaw; and/or a guide as described above.

It is a fifth aspect of the present disclosure to provide a method of using a surgical device, the method including positioning an elongate, flexible guide proximate a heart so that the guide extends from a first end portion of the guide, right to left through the transverse sinus, inferiorly proximate the left pulmonary veins, left to right through the oblique sinus, and to a second end portion of the guide; coupling the first end portion of the guide to a tip of a first jaw of a clamp; coupling the second end portion of the guide to a tip of a second jaw of a clamp; positioning the first jaw and the second jaw proximate the left atrium by pulling the guide generally right to left and anteriorly; and/or clamping a portion of the left atrium between the first jaw and the second jaw.

In a more detailed embodiment of the fifth aspect, the method may include, after clamping the portion of the left atrium, at least partially ablating the portion of the left atrium between the first jaw and the second jaw. Ablating the portion of the left atrium between the first jaw and the second jaw may include applying bipolar radio frequency energy to the portion of the left atrium between the first jaw and the second jaw using a first electrode and a second electrode arranged generally in parallel on the first jaw and a third electrode and a fourth electrode arranged generally in parallel on the second jaw.

In a more detailed embodiment of the fifth aspect, positioning the elongate, flexible guide proximate the heart may include positioning the guide proximate the heart so that the guide extends from the first end portion of the guide, left to right through the oblique sinus, superiorly proximate the right pulmonary veins, right to left through the transverse sinus, and to the second end portion of the guide; releasably coupling the first end portion to the second end portion to form the guide into a closed loop; moving the guide so that the guide extends from the releasably coupled first end portion and second end portion, right to left through the transverse sinus, inferiorly proximate the left pulmonary veins, left to right through the oblique sinus, and to the releasably coupled first end portion and second end portion; and/or uncoupling the first end portion from the second end portion. Releasably coupling the first end portion to the second end portion may include releasably magnetically coupling a first permanent magnet disposed at the first end portion of the guide with a second permanent magnet disposed at the second end portion of the guide.

In a more detailed embodiment of the fifth aspect, the clamp may include a handle, a shaft extending distally from the handle, and an end effector disposed at a distal end of the shaft, the end effector comprising the first jaw and the second jaw. Positioning the first jaw and the second jaw proximate the left atrium may include positioning the first jaw at least partway through the transverse sinus and positioning the second jaw at least partway through the oblique sinus. Clamping the portion of the left atrium between the first jaw and the second jaw may include clamping a portion of the left atrium circumscribing the right pulmonary veins. The method may include ablating the portion of the left atrium circumscribing the right pulmonary veins between the first jaw and the second jaw. The method may include clamping a portion of the left atrium circumscribing the left pulmonary veins between the first jaw and the second jaw and/or ablating the portion of the left atrium circumscribing the left pulmonary veins between the first jaw and the second jaw. The portion of the left atrium circumscribing the right pulmonary veins and/or the portion of the left atrium circumscribing the left pulmonary veins may not be overlapping and/or the respective ablating operations may form spaced-apart pulmonary vein isolation lesions. The portion of the left atrium circumscribing the right pulmonary veins and/or the portion of the left atrium circumscribing the left pulmonary veins may overlap between the right pulmonary veins and/or the left pulmonary veins and/or the respective ablating operations may form a figure-8 lesion.

In a more detailed embodiment of the fifth aspect, clamping the portion of the left atrium between the first jaw and the second jaw may include clamping the left atrium so that the portion of the left atrium between the first jaw and the second jaw simultaneously circumscribes the right pulmonary veins and the left pulmonary veins. The method may include, after clamping the portion of the left atrium, at least partially ablating the portion of the left atrium between the first jaw and the second jaw. Ablating the portion of the left atrium between the first jaw and the second jaw may include forming a complete box lesion around the right pulmonary veins and the left pulmonary veins in a single ablating operation without repositioning the first jaw and/or the second jaw.

In a more detailed embodiment of the fifth aspect, coupling the first end portion of the guide to the tip of the first jaw of the clamp may include releasably coupling the first end portion of the guide to the tip of the first jaw of a clamp. Coupling the second end portion of the guide to the tip of the second jaw of the clamp may include releasably coupling the second end portion of the guide to the tip of the second jaw of the clamp.

In a more detailed embodiment of the fifth aspect, the clamp may include a shaft, a handle disposed proximally on the shaft, and/or an end effector disposed distally on the shaft, the end effector including the first jaw and/or the second jaw. Positioning the first jaw and/or the second jaw proximate the left atrium may include positioning the shaft in a generally anterior to posterior direction along the right lateral aspect of the heart. The clamp may include a shaft, a handle disposed proximally on the shaft, and/or an end effector disposed distally on the shaft, the end effector including the first jaw and/or the second jaw. Clamping a portion of the left atrium between the first jaw and the second jaw may include operating an actuator on the handle, the actuator being operatively coupled to move the first jaw from an open position to a closed position.

BRIEF DESCRIPTION OF THE DRAWINGS

Example embodiments are described in conjunction with the accompanying drawing figures in which.

DETAILED DESCRIPTION

Example embodiments according to the present disclosure are described and illustrated below to encompass devices, methods, and techniques relating to medical procedures. Of course, it will be apparent to those of ordinary skill in the art that the embodiments discussed below are examples and may be reconfigured without departing from the scope and spirit of the present disclosure. It is also to be understood that variations of the example embodiments contemplated by one of ordinary skill in the art shall concurrently comprise part of the instant disclosure. However, for clarity and precision, the example embodiments as discussed below may include optional steps, methods, and features that one of ordinary skill should recognize as not being a requisite to fall within the scope of the present disclosure.

The present disclosure includes, inter alia, medical instruments and devices and related methods, and, more specifically, surgical devices for clamping and ablating tissue and related methods. Some example embodiments according to at least some aspects of the present disclosure may be particularly useful in connection with ablation of cardiac tissue, such as to treat cardiac arrhythmias like atrial fibrillation, for the reasons discussed above in the Introduction section and the patent references incorporated by reference herein.

Figure 1:
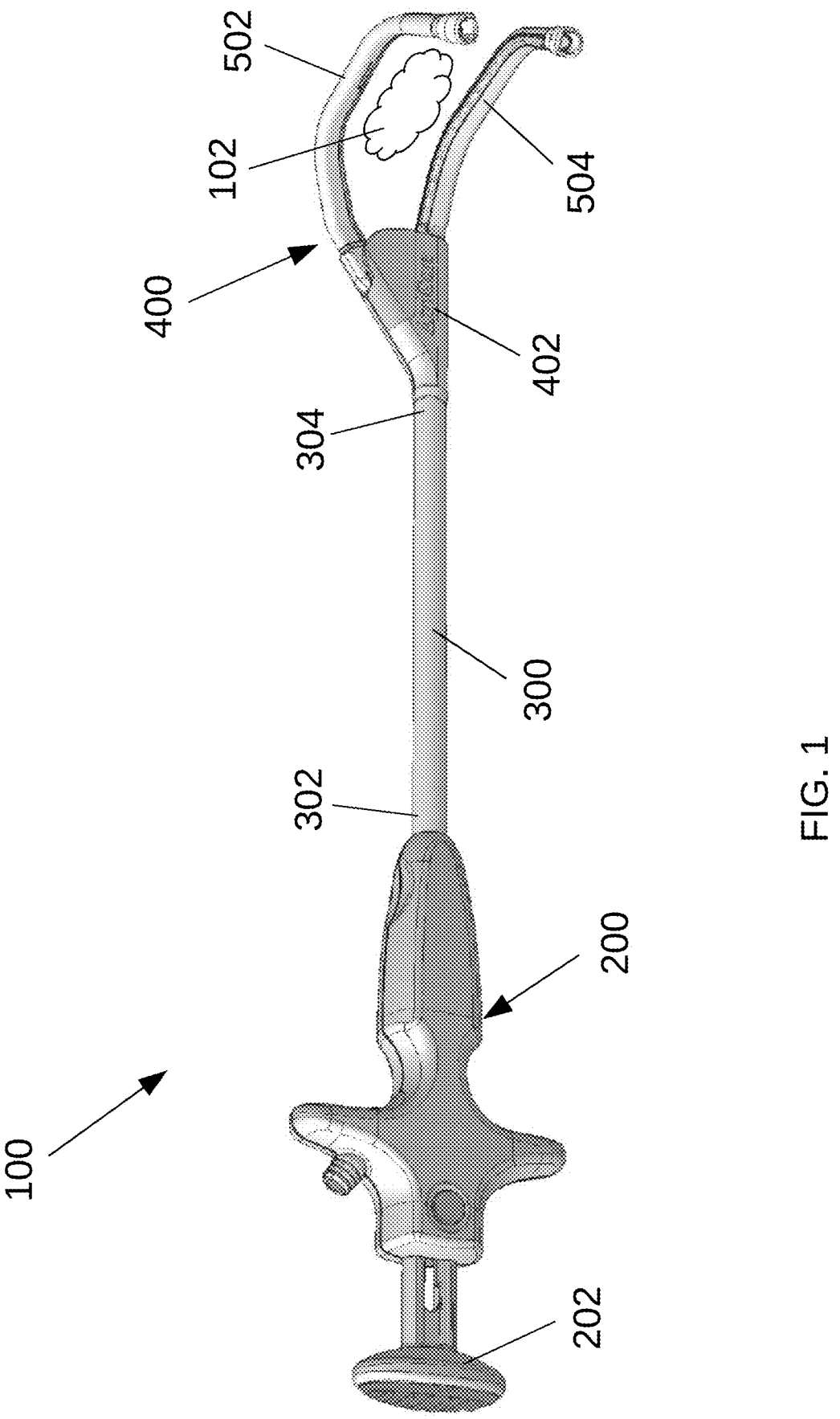
FIG. 1 is a perspective view of an example surgical device.

FIG. 1 is a perspective view of an example surgical device, such as a surgical clamp 100, according to at least some aspects of the present disclosure. In some example embodiments, the surgical clamp 100 may include a handle 200 disposed at a proximal end 302 of a generally elongated shaft 300. An end effector 400 may be disposed at a distal end 304 of the shaft 300. The end effector 400 may include one or more jaws, such as a first jaw 502 and/or a second jaw 504, which may be disposed generally distally on a head 402. The handle 200 may include an actuator, such as a plunger 202, which may be operative to move the first jaw 502 and/or the second jaw 504 relative to the head 402, such as to close on (e.g., clamp) a target tissue 102.

As used herein, "proximal" may refer generally to the direction towards the handle 200 end of the surgical clamp 100. As used herein, "distal" may refer generally to the direction towards the end effector 400 end of the surgical clamp 100.

Figures 2, 3, 4, 5:
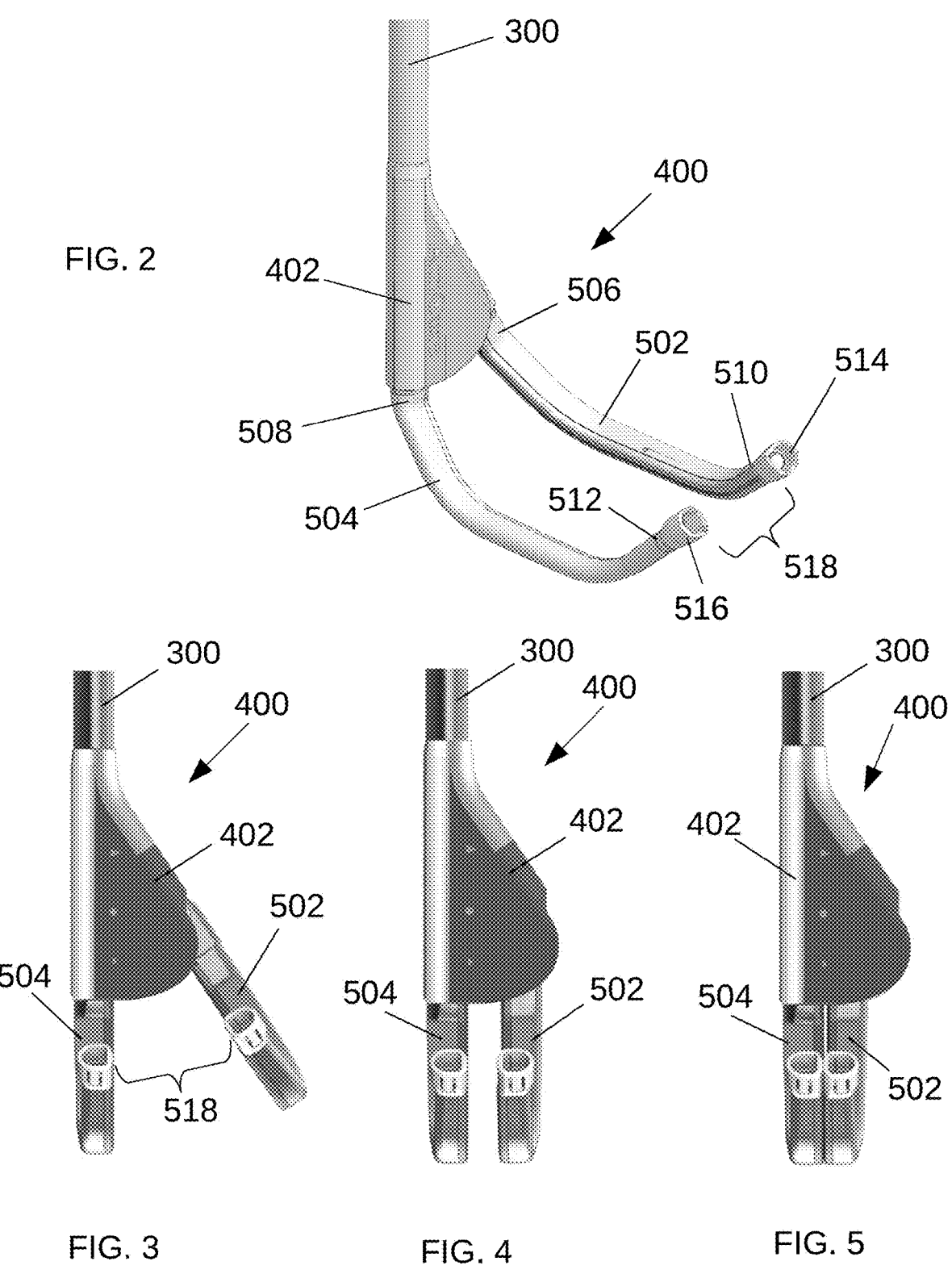
FIG. 2 is a detailed perspective view of an example end effector.
FIG. 3 is a side view of an example end effector with the jaws in an open position.
FIG. 4 is a side view of an example end effector with the jaws in an intermediate position.
FIG. 5 is a side view of an example end effector with the jaws a closed position.

FIG. 2 is a detailed perspective view of an example end effector 400, according to at least some aspects of the present disclosure. Each of the first jaw 502 and the second jaw 504 may include a respective first end portion 506, 508 proximate the head 402 and a respective second end portion 510, 512 generally away from the head 402. Each of the second end portions 510, 512 may terminate at a respective tip 514, 516. In the open position of FIG. 2, the jaws 502, 504 may define an open mouth 518 between the spaced-apart tips 514, 516.

FIG. 3 is a side view of an example end effector 400 with the jaws 502, 504 in an open position, FIG. 4 is a side view of an example end effector 400 with the jaws 502, 504 in an intermediate position, FIG. 5 is a side view of an example end effector 400 with the jaws 502, 504 in a closed position, all in accordance with at least some aspects of the present disclosure.

Referring to FIGS. 1-3, in the open position, the first jaw 502 and second jaw 504 may be separated and may be substantially non-parallel. Referring to FIG. 4, in the intermediate position, the first jaw 502 and the second jaw 504 may be separated and may be substantially parallel. Referring to FIG. 5, in the closed position, the first jaw 502 and the second jaw 504 may be substantially adjacent and may be substantially parallel. As used herein with reference to the jaws 502, 504 in the closed position, "substantially adjacent" may include a small gap between the jaws 502, 504, such as due to the thickness of the target tissue 102 (FIG. 1), which may be clamped between the jaws 502, 504.

Referring to FIGS. 3-5, movement of the first jaw 502 from the open position (FIG. 3) to the intermediate position (FIG. 4) may include a substantial angular change (e.g., pivoting or rotating) with respect to the head 402, such as about an axis of rotation that is generally perpendicular to the shaft 300. Movement of the first jaw 502 from the intermediate position (FIG. 4) to the closed position (FIG. 5) may include a substantial translation with respect to the head 402, such as while the first jaw 502 and the second jaw 504 remain substantially parallel.

In some example embodiments, the first jaw 502 may be movable with respect to the head 402 while the second jaw 504 may be fixed (e.g., rigid) with respect to the head 402. In some circumstances, having one rigid jaw 504 may be advantageous because it may provide the surgeon with a fixed, known point of reference when positioning the clamp 100 (FIG. 1). In other example embodiments, both the first jaw 502 and the second jaw 504 may be movable with respect to the head 402. For purposes of clarity and brevity, the description herein focuses on the movement of the first jaw 502 and the associated components facilitating such movement. A person of skill in the art will understand, however, that substantially similar components may be used to facilitate movement of the second jaw 504, thereby providing an alternative example embodiment in which both the first jaw 502 and the second jaw 504 may be movable with respect to the head 402 between the open position, the intermediate position, and the closed position, and such an embodiment is within the scope of this disclosure.

In some example embodiments, the shaft 300 may be substantially rigid. In other example embodiments, at least a portion of the shaft 300 may be bendable or malleable (e.g., plastically deformable), which may allow a user to configure the shaft 300 to accommodate a patient's specific anatomy. In some example embodiments, the shaft may be substantially straight (e.g., linear). In other example embodiments, the shaft 300 may include at least one curved portion. For example, the shaft 300 may be generally C-shaped (e.g., one curve) or S-shaped (e.g., two curves in opposite directions).

Figure 6:
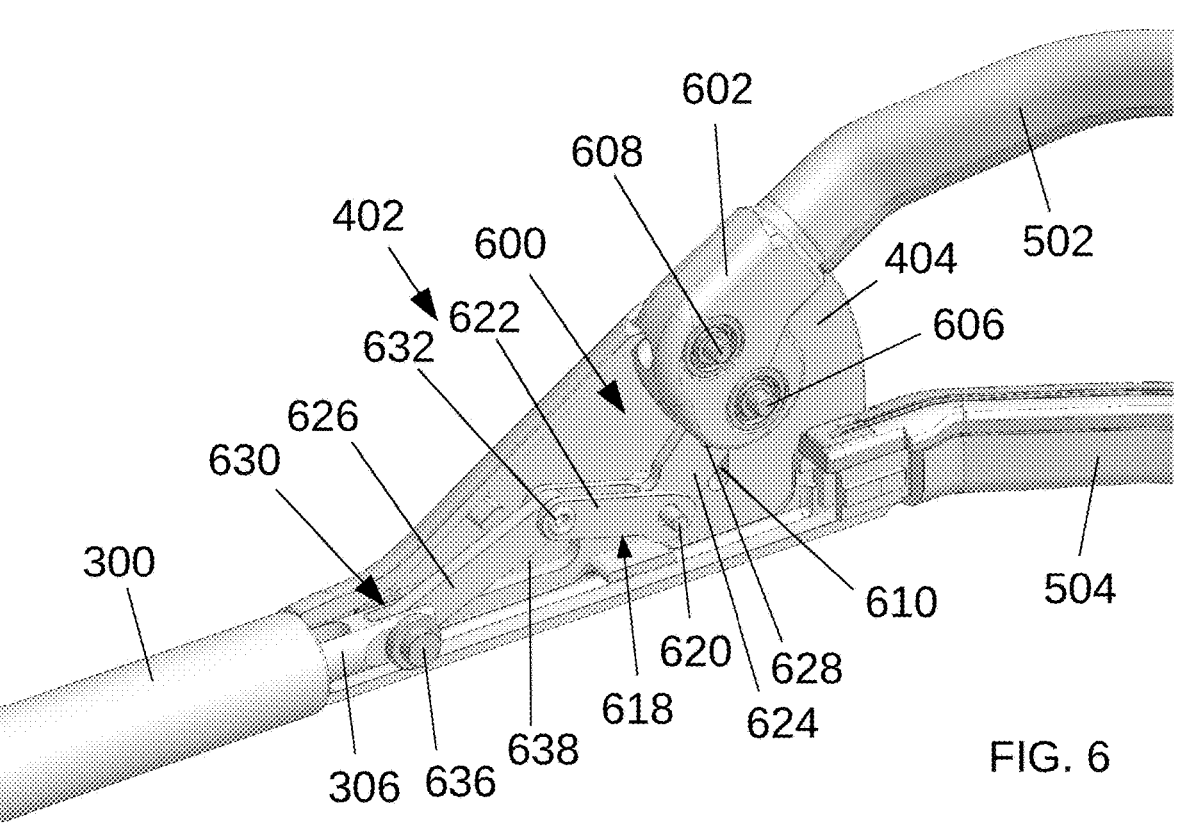
FIGS. 6 and 7 are perspective cutaway views of an example articulating mechanism.
Figure 7:
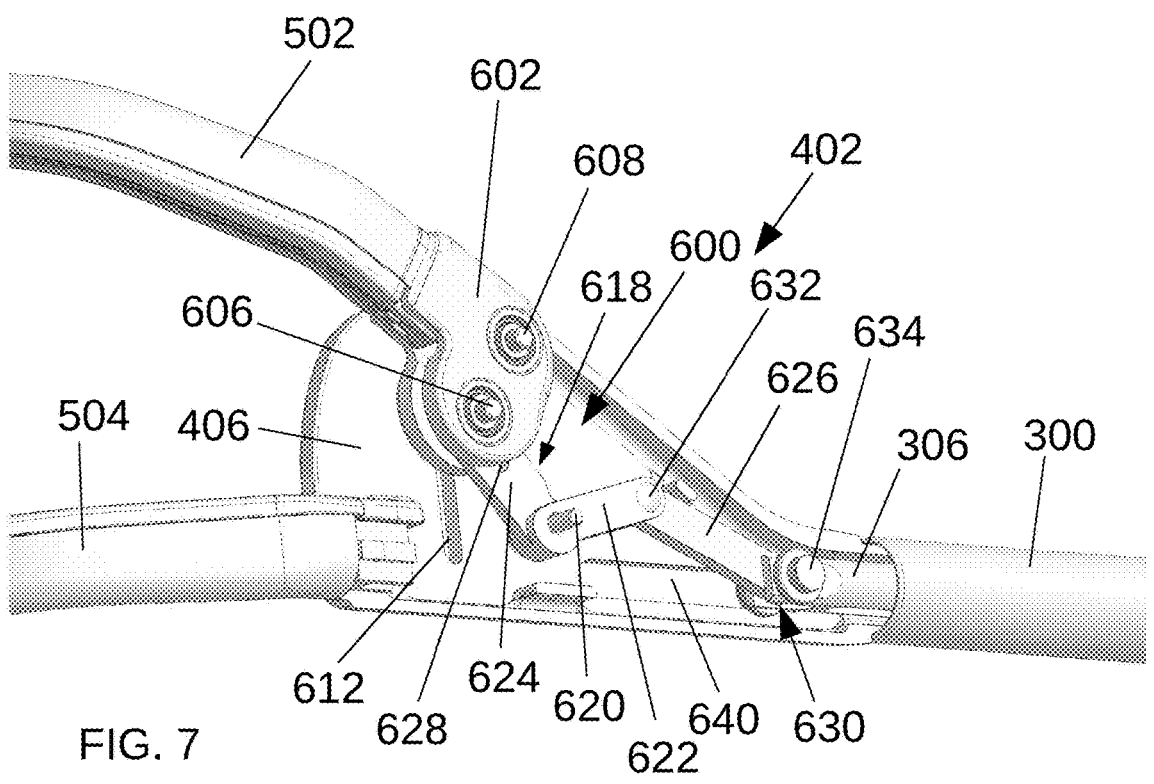
Figure 8:
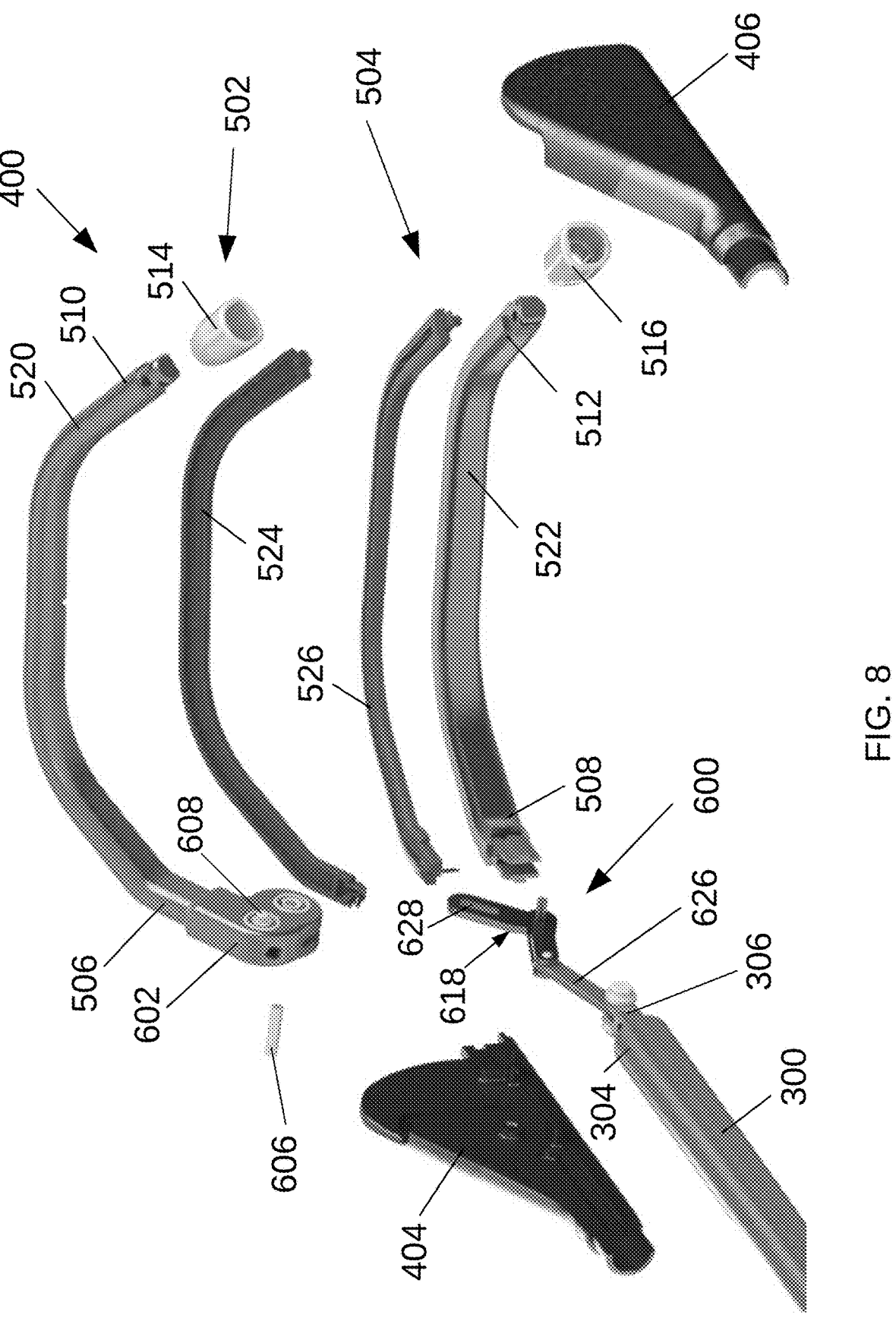
FIG. 8 is an exploded perspective view of an example end effector including an example articulating mechanism.
Figure 9:
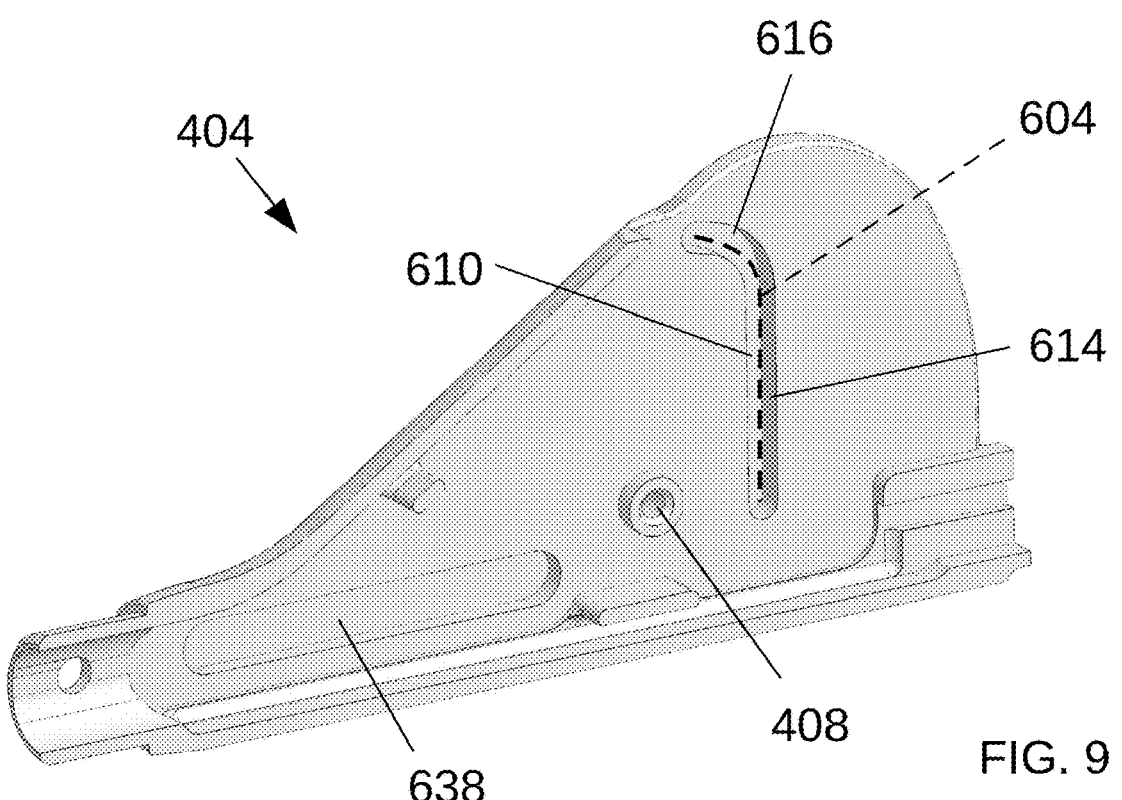
FIGS. 9 and 10 are detailed internal perspective views of example head shell portions.
Figure 10:
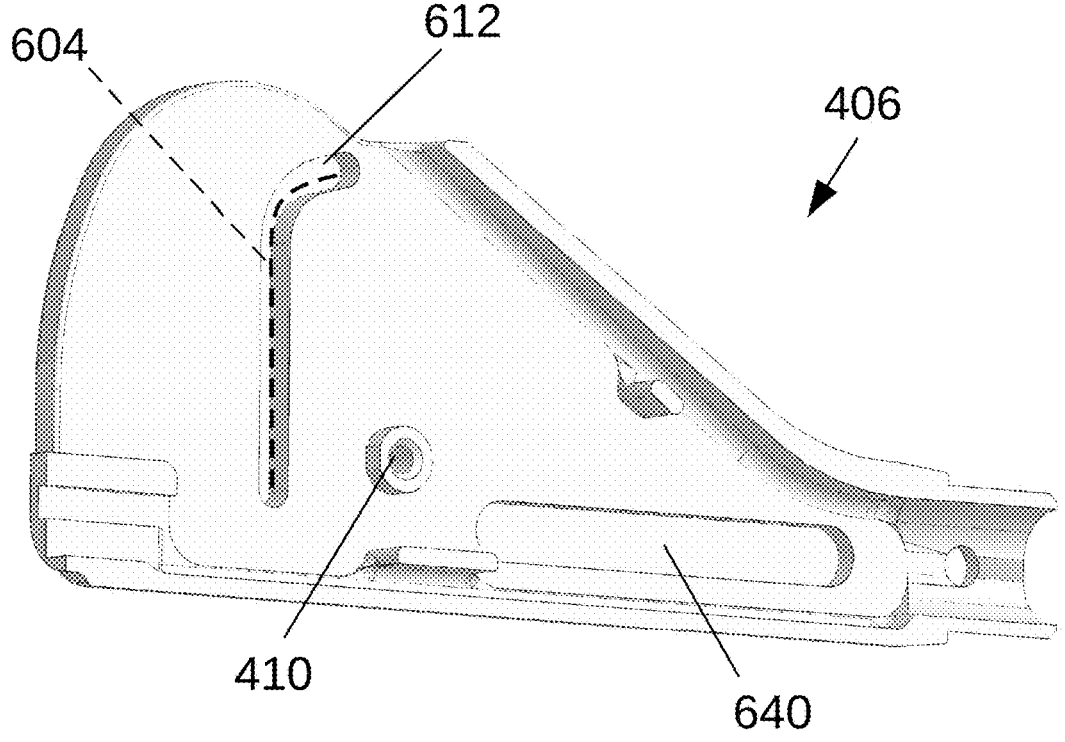

FIGS. 6 and 7 are perspective cutaway views of an example articulating mechanism 600 (FIGS. 6 and 7 are different side perspective views of the same example device), FIG. 8 is an exploded perspective view of an example end effector 400 including an example articulating mechanism 600, FIGS. 9 and 10 are detailed internal perspective views of example head shell portions 404, 406, all according to at least some aspects of the present disclosure. Generally, the articulating mechanism 600 may be operable to move the first jaw 502 between the open position, the intermediate position, and the closed position upon operation of the actuator 202 (FIG. 1) by the user. In embodiments including a movable second jaw 504, a similar articulating mechanism may be utilized in connection with the second jaw 504.

Referring to FIGS. 6-10, an example articulating mechanism 600 may include a first jaw mount 602, which may be coupled (e.g., rigidly affixed) to the first jaw 502. In some example embodiments, the first jaw mount 602 may be integrally formed with at least a portion of the first jaw 502, such as is shown in FIG. 8. In other embodiments, the first jaw 502 may be affixed to a separate component comprising the first jaw mount 602.

In some example embodiments, the first jaw mount 602 may be movable along a path 604 (FIGS. 9 and 10) with respect to the head 402, which may cause rotation and/or translation of the first jaw mount 602 and the first jaw 502 between the open position, the intermediate position, and/or the closed position. For example, the first jaw 502 may rotate about 45 degrees between the open position and the intermediate position and/or the first jaw may translate about 10 mm between the intermediate position and the closed position. For example, the first jaw mount 602 may include a first pin 606 and/or a second pin 608, which may be slidably and/or rotatably movable along the path 604, which may be at least partially defined one or more slots. For example, the path 604 may be at least partially defined by a slot 610 on an internal surface of the shell portion 404 of the head 402 and/or the path 604 may be at least partially defined by a slot 612 on an internal surface of the shell portion 406 of the head 402. Although the illustrated embodiment utilizes pins 606, 608 movable within slots 610, 612 to facilitate movement of the first jaw mount 602 along the path 604, it is within the scope of the disclosure to utilize other components and/or mechanisms, such as tracks, rollers, sliders, etc. to facilitate movement of the first jaw mount 602 along the path 604.

Referring to FIGS. 9 and 10, in some example embodiments, the path 604 (and/or the slots 610, 612) may comprise at least one generally straight portion 614 and/or at least one generally curved portion 616. In some embodiments including two pins 606, 608 moving along the path 604 defined by slots 610, 612, the generally curved portion 616 may be operable cause the first jaw mount 602 (and attached first jaw 502) to pivot or rotate substantially with respect to the head 402. The length, orientation, and/or curvature of the generally curved portion 616 may establish the extent of the angular rotation of the first jaw mount 602 and/or the amount of translation of the first jaw mount 602 with respect to the head 402. Similarly, in some embodiments including two pins 606, 608 moving along the path 604 defined by slots 610, 612, the generally straight portion 616 may be operable to cause the first jaw mount 602 (and attached first jaw 502) to translate with respect to the head 402 without substantially changing the angle of the first jaw mount 602 with respect to the head 402. The length and/or orientation of the generally straight portion 614 may establish the extent of the translation of the first jaw mount 602 with respect to the head 402. It is within the scope of this disclosure to utilize any combination of generally curved portions 616 and/or generally straight portions 614 to provide a desired path 604 to obtain a desired movement of the first jaw mount 602 (and attached first jaw 502). For example, an alternative path may include a continuous curve that varies in curvature over its length. Or, for example, an alternative path may include two generally straight portions 614 interposed by a curved portion 616.

Referring to FIGS. 6-10, in some example embodiments, the articulating mechanism 600 may include a crank 618 pivotably mounted with respect to the head 402. For example, the crank 618 may be pivotably disposed within the head 402, such as by a pivot pin 620 received in pivot holes 408, 410 of the shell portions 404, 406, respectively. The crank 618 may be operably coupled to the first jaw mount 602 to move the first jaw mount 602 along the path 604. For example, rotation of the crank 618 may cause the first jaw mount 602 to move along the path 604.

In some example embodiments, the crank 618 may include a first arm 622, which may be operably coupled to an actuator linkage 306, and/or a second arm 624, which may be operably coupled to the first jaw mount 602. The actuator 202 (FIG. 1) may be operably coupled to the actuator linkage 306, which may extend generally longitudinally through the shaft 300. Some example embodiments may include a connecting linkage 626 interposing the actuator linkage 306 and the crank 618. The articulating mechanism 600 may be configured so that movement of the actuator 202 causes rotation of the crank 618 (e.g., via the actuator linkage 306 and/or the connecting linkage 626). As the crank 618 rotates, the second arm 624 may move the first jaw mount 602 along the path 604 to move the first jaw 502 between the open position, the intermediate position, and/or the closed position.

Although the crank 618 of the illustrated embodiment comprises two, generally separately extending arms 622, 624, it is within the scope of the disclosure to utilize a crank with arms that are not substantially separately formed. For example, such a crank may be generally in the form of a circular sector of about 120 degrees in which the area between the arms is at least partially continuous. In some example embodiments, connecting the arms 622, 624 together at positions radially distant from the axis of rotation may increase the strength of the crank 618, thereby increasing the maximum allowable torque and/or forces for a given material and thickness. In some example embodiments, varying the effective lengths of the arms 622, 624 (e.g., the radial distances between the pivot pin 620 and the first pin 606 and/or the pivot pin 620 and the pivotable connection

632 (described below)) may facilitate varying the maximum allowable torque and/or force.

In some example embodiments, the distance between the pivot axis of the crank 618 (e.g., pivot pin 620) and the path 604 (along which the first pin 606 moves) may vary over the length of the path 604. Accordingly, the second arm 624 of the crank 618 may be slidably and/or pivotably coupled to the first jaw mount 602. For example, the second arm 624 of the crank 618 may include a crank slot 628, which may slidably and/or pivotably receive the first pin 606 of the first jaw mount 602 so that the first pin 606 moves along the crank slot 628 as the first jaw mount 602 moves along the path 604. In some example embodiments, the crank slot 628 may be substantially straight and/or may be oriented substantially radially with respect to the axis of rotation of the crank 618 (e.g., pivot pin 620).

In some example embodiments including a connecting linkage 626, a proximal end of the connecting linkage 626 may be coupled to a distal end of the actuator linkage 306 by a pivotable connection 630. A distal end of the connecting linkage 626 may be coupled to the first arm 622 of the crank by a pivotable connection 632. The pivotable connection 630 between the distal end of the actuator linkage 306 and the proximal end of the connecting linkage 626 may include one or more guides 634, 636, which may be slidable within respective guide slots 638, 640 on internal surfaces of the shell portions 404, 406 of the head 402. In some example embodiments, the guide slots 638, 640 may be generally linear and/or may be positioned substantially axially with respect to the shaft 300 so that the actuator linkage 306 moves generally proximally and distally in substantially a straight line (e.g., generally in-line with the actuator linkage 306).

Figure 11:
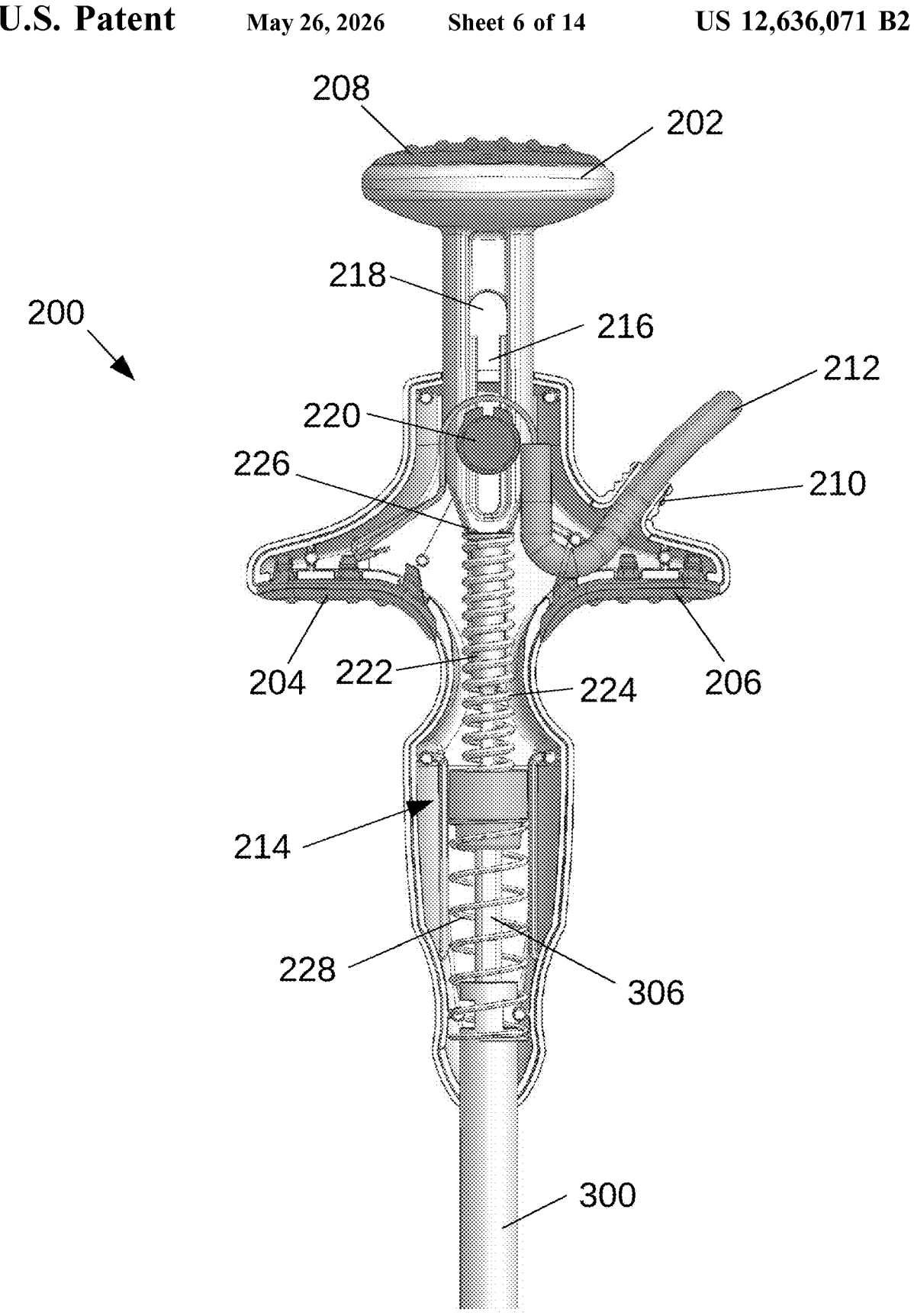
FIG. 11 is an internal side view of an example handle.

FIG. 11 is an internal side view of an example handle 200, according to at least some aspects of the present disclosure. Generally, the handle 200 may be constructed and/or may operate as described in U.S. Pat. No. 8,876,820, which is incorporated by reference. The handle 200 may include grips 204, 206, 208. The handle 200 may include a port 210 through which wires 212 or tubes may extend from the interior to the exterior of the handle 200. For instance, wires 212 for ablation electrodes or sensors on the jaws 502, 504 may be routed through the shaft 300, into the handle 200, and out through the port 210.

In some example embodiments, the handle 200 may house an actuator mechanism 214. In this example embodiment, the plunger 202 may be used to articulate one or more of the jaws 502, 504. The plunger 202 may be generally aligned with the shaft 300. With the plunger 202 in the fully retracted or proximal position, the first jaw 502 may be in the open position (FIG. 3). When the plunger 202 is depressed in the distal direction, the first jaw 502 may move from the open position (FIG. 3) to the intermediate position (FIG. 4). Further depression of the plunger 202 may move the first jaw 502 from the intermediate position (FIG. 4) to the closed position (FIG. 5).

In some example embodiments, the actuator mechanism 214 may include a locking mechanism. For example, the plunger 202 may include a generally longitudinal slot 216 with a widened proximal opening 218. When the jaws 502, 504 are in the closed position, the opening 218 may align with a lock button 220, which may be spring-biased to drive the lock button 220 into the opening 218, thereby preventing the plunger 202 from moving proximally and maintaining the jaws 502, 504 in the closed position. Depressing the lock button 220 may disengage the lock button 220 from the opening 218, thereby releasing the plunger 202 and allowing it to move proximally to open the jaws 502, 504.

In some example embodiments, the actuator mechanism 214 may be configured to control and/or limit the amount of force that may be applied by the jaws 502, 504 when the plunger 202 is depressed. For example, the actuator mechanism 214 may include a relief rod 222 and a force limiting spring 224. The relief rod 222 may be slidable with respect to the actuator linkage 306, while the force limiting spring 224 may be arranged to apply a distal force to the actuator linkage 306. As the plunger 202 is depressed, the force limiting spring 224 may compressed between a step 226 on the plunger 202 and the actuator linkage 306. Accordingly, depressing the actuator 202 imparts a load on the force limiting spring 224 that is transferred to the actuator linkage 306, which moves the actuator linkage 306 distally. If the jaw clamping load exceeds the desired maximum while the plunger 202 continues to be depressed, the force limiting spring 224 is further compressed and the relief rod 222 moves distally without moving the actuator linkage 306. Thus, the force limiting spring 224 substantially limits the maximum jaw clamping load. One with ordinary skill in the art will recognize that the tissue clamping pressure may be a function of the jaw clamping force and the tissue area being clamped. The actuator mechanism 214 may include a return spring 228 that may be operative to move the actuator linkage 306 proximally upon releasing the actuator 202.

Figure 12:
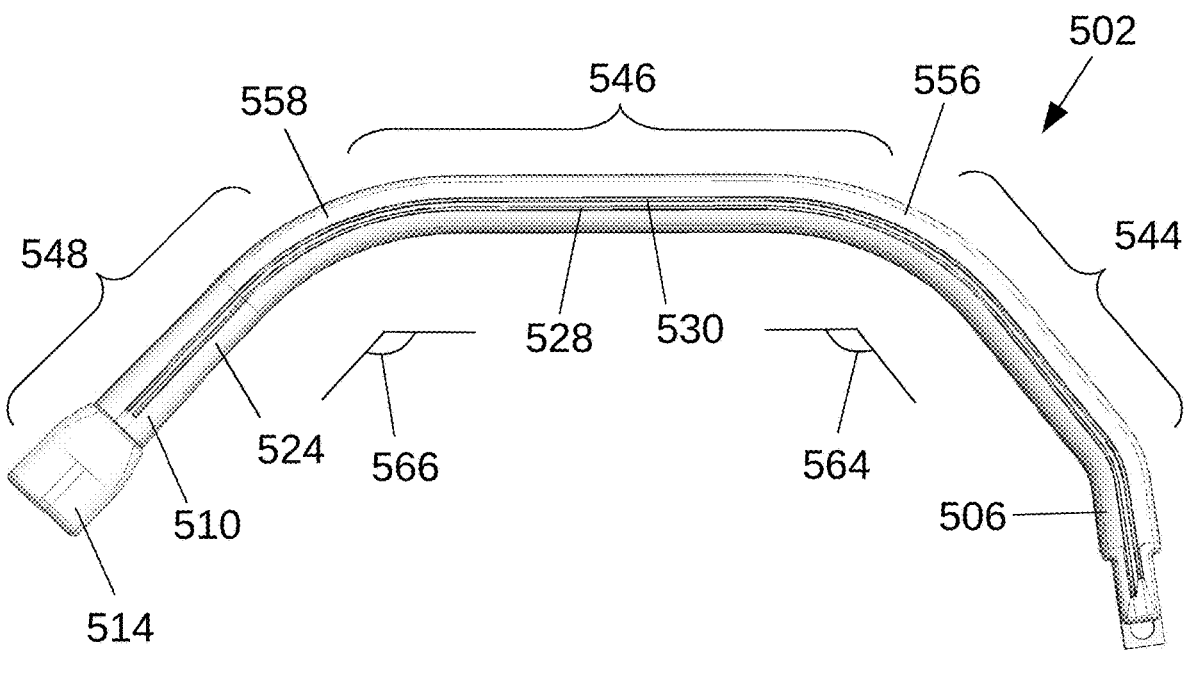
FIG. 12 is a detailed view of the inwardly facing (e.g., tissue-clamping) surface of an example first jaw.
Figure 13:
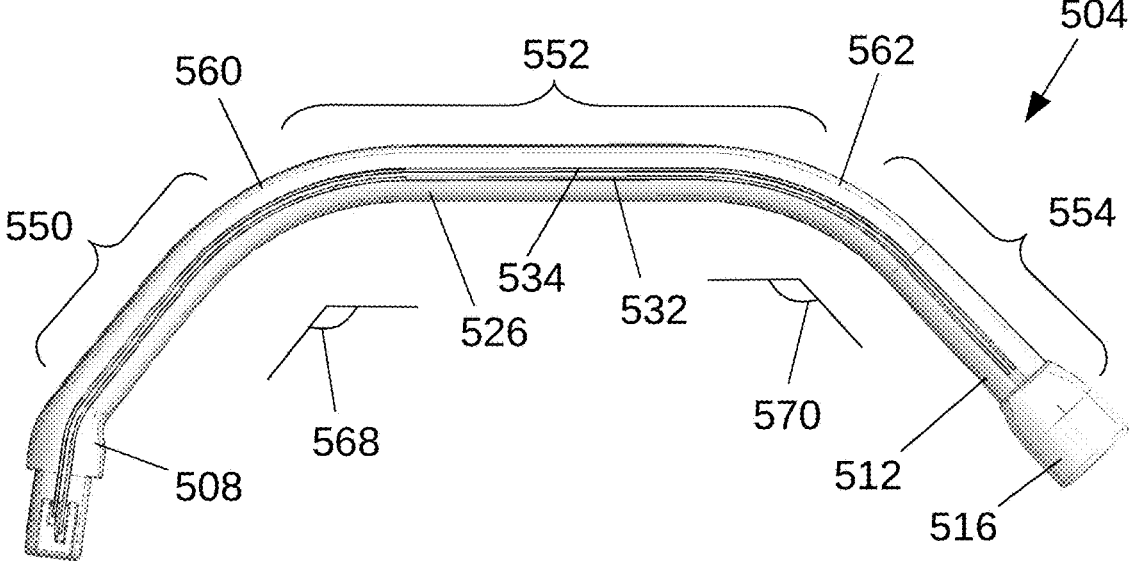
FIG. 13 is a detailed view of the inwardly facing (e.g., tissue-clamping) surface of an example second jaw.
Figures 14, 15:
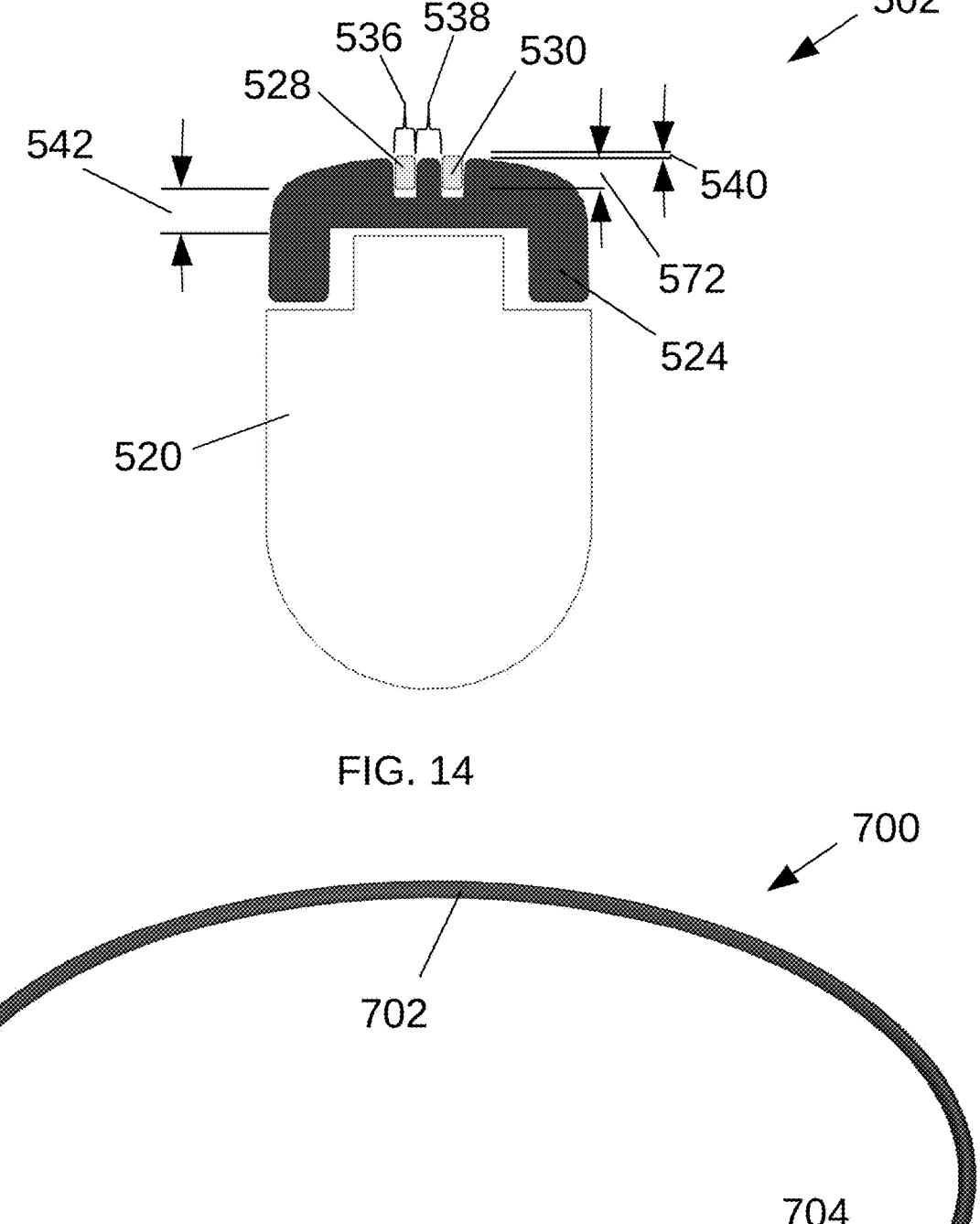
FIG. 14 is a cross-sectional view of an example first jaw.
FIG. 15 is a perspective view of an example guide.

FIG. 12 is a detailed view of the inwardly facing (e.g., tissue-clamping) surface of an example first jaw 502, FIG. 13 is a detailed view of the inwardly facing (e.g., tissue-clamping) surface of an example second jaw 504, and FIG. 14 is a cross-sectional view of an example first jaw 502, all according to at least some aspects of the present disclosure. Although FIG. 14 illustrates certain components and dimensions associated with the first jaw 502, the second jaw 504 may include similar components with similar dimensions unless otherwise specifically indicated.

Referring to FIGS. 2, 8, and 12-14, in some example embodiments, the first jaw 502 may comprise a substantially rigid jaw beam 520 extending generally from the proximal end portion 506 (e.g., proximate the first jaw mount 602) to the distal end portion 510 (e.g., proximate the tip 514). Similarly, the second jaw 504 may comprise a substantially rigid jaw beam 522 extending generally from the proximal end portion 508 to the distal end portion 512 (e.g., proximate the tip 516). The jaw beams 520, 522 may be constructed from stainless steel, for example, which may provide the desired bending strength as well as acting as a heat sink during some procedures involving ablation. Other biocompatible materials providing suitable mechanical and thermal characteristics, such as other metals (e.g., aluminum), may be used for alternative jaw beams.

In some example embodiments, an insulator 524, 526 may be disposed on each respective jaw, such as on the inwardly facing surface of each respective jaw beam 520, 522. The insulators 524, 526 may be constructed of an electrically non-conductive material, such as molded plastic. Other biocompatible materials providing suitable insulative and thermal characteristics may be used for alternative insulators.

In some example embodiments, such as those configured for radio frequency (RF) ablation, the jaws 502, 504 may include one or more electrodes, which may be disposed on (e.g., mounted at least partially within) the insulators 524, 526. For example, electrodes may be bonded to or overmolded in the insulators 524, 526. The first jaw may include one or more elongated, spaced apart electrodes: first electrode 528 and/or second electrode 530. Similarly, the second jaw may include one or more elongated, spaced apart electrodes: third electrode 532 and/or fourth electrode 534. In some example embodiments, the electrodes 528, 530, 532, 534 may be configured to conduct bipolar, radio-frequency ablation of target tissue 102 clamped between the jaws 502, 504. Each electrode 528, 530, 532, 534 may have a width 536, which may be the width of the tissue-facing surface in a direction generally perpendicular to the local, elongated direction of the electrode. In embodiments including more than one electrode 528, 530, 532, 534 per jaw 502, 504, the electrodes 528, 530, 532, 534 may be spaced apart by an electrode spacing 538. Each electrode 528, 530, 532, 534 may extend beyond the surface of the insulators 524, 526 by a projection height 540. Each electrode 528, 530, 532, 534 may be spaced disposed at an insulation depth 542 from its respective jaw beam 520, 522. Each electrode 528, 530, 532, 534 may have an electrode height 572.

In some example embodiments, the electrode width 536 may be about 0.1 mm to about 2.0 mm. In some example embodiments, the electrode width 536 may be about 0.2 to about 0.4 mm. In the example embodiment shown in FIGS. 12-14, the electrode width 536 may be about 0.30 mm. In some example embodiments, each electrode 528, 530, 532, 534 may have substantially the same width 536, which may be substantially constant over the length each electrode 528, 530, 532, 534. In other embodiments, the width 536 may vary over the length of an electrode 528, 530, 532, 534 and/or may differ from electrode 528, 530, 532, 534 to electrode 528, 530, 532, 534.

In some example embodiments, the electrode spacing 538 may be about 0.1 mm to about 3.0 mm. In some example embodiments, the electrode spacing 538 may be about 0.3 mm to about 0.6 mm. In the example embodiment shown in FIGS. 12-14, the electrode spacing 538 may be about 0.43 mm. In some example embodiments, the electrode spacing 538 may be substantially constant over the length of the plurality of electrodes 528, 530, 532, 534 so that the electrodes 528, 530, 532, 534 are substantially parallel in any local region. In other embodiments, the electrode spacing 538 may vary over the length of the plurality of electrodes 528, 530, 532, 534 so that the electrodes 528, 530, 532, 534 may be closer together in some regions and/or farther apart in other regions.

In some example embodiments, the projection height 540 may be about 0.0 mm (e.g., flush) to about 0.5 mm. In some example embodiments, the projection height 540 may be about 0.1 mm to about 0.2 mm. In the example embodiment shown in FIGS. 12-14, the projection height 540 may be about 0.15 mm. In some example embodiments, the projection height 540 may be substantially constant over the length of a particular electrode 528, 530, 532, 534 and/or may be substantially the same for two or more electrodes 528, 530, 532, 534. In other embodiments, the projection height 540 may vary over the length of an electrode 528, 530, 532, 534 and/or from electrode 528, 530, 532, 534 to electrode 528, 530, 532, 534.

In some example embodiments, the insulation depth 542 may be about 0.1 mm to about 5.0 mm. In some example embodiments, the insulation depth 542 may be about 0.8 mm to about 1.6 mm. In the example embodiment shown in FIGS. 12-14, the insulation depth 542 may be about 1.25 mm. In some example embodiments, the insulation depth 542 may be substantially constant over the length of a particular electrode 528, 530, 532, 534 and/or may be substantially the same for two or more electrodes 528, 530, 532, 534. In other embodiments, the insulation depth 542 may vary over the length of an electrode 528, 530, 532, 534 and/or from electrode 528, 530, 532, 534 to electrode 528, 530, 532, 534.

In some example embodiments, the electrode height 572 may be about 0.25 mm to about 3.0 mm. In some example embodiments, the electrode height 572 may be about 0.3 mm to about 0.7 mm. In the example embodiment shown in FIGS. 12-14, the electrode height 572 may be about 0.5 mm. In some example embodiments, the electrode height 572 may be substantially constant over the length of a particular electrode 528, 530, 532, 534 and/or may be substantially the same for two or more electrodes 528, 530, 532, 534. In other embodiments, the electrode height 572 may vary over the length of an electrode 528, 530, 532, 534 and/or from electrode 528, 530, 532, 534 to electrode 528, 530, 532, 534.

In some example embodiments, the electrodes 528, 520, 532, 534 may extend substantially the entire length of the jaws 502, 504 between the head 402 and the tips 514, 516. In the example embodiment shown in FIGS. 2, 12, and 13, the electrodes 528, 520, 532, 534 may be about 105 mm long. In an alternative example embodiment with shorter jaws, the electrodes 528, 520, 532, 534 may be about 86 mm long.

U.S. Pat. No. 9,924,998, titled "Ablation System, Clamp and Method of Use," issued Mar. 27, 2018, is incorporated by reference and describes various apparatus and methods related to tissue ablation using radio-frequency energy, some of which may be used in connection with some example embodiments according to at least some aspects of the present disclosure. Generally, reducing the electrode spacing 538 may result in narrower lesions and/or faster ablation. Generally, increasing the insulation depth 542 may result in narrower lesions, faster ablation, and/or lower energy per unit volume.

In some example embodiments according to at least some aspects of the present disclosure, the jaws 502, 504 of the clamp 100 may be configured to facilitate positioning adjacent to and engagement of a particular target tissue 102 in a desired manner. For example, the shape of the jaws 502 between the first end portions 506, 508 near the head 402 and the tips 514, 516 may be selected based on the target tissue 102 and/or the location of the target tissue 102 in relation other anatomical structures. As described in detail below, some example clamps 100 may be used to create lesions around the pulmonary veins, which are located generally on the posterior portion of the heart. When the heart is accessed via a median sternotomy, creating lesions around the pulmonary veins may require positioning the clamp 100 at least partially around the posterior aspect of the heart, while engaging the left atrium and avoiding nearby structures that will not be ablated.

Referring to FIGS. 12 and 13, in some example embodiments, the jaws 502, 504 may be formed of one or more substantially straight (e.g., generally linear) portions 544, 546, 548, 550, 552, 554, which may be interposed by one or more generally curved or bent portions 556, 558, 560, 562. For example, in the first jaw 502, a first substantially straight portion 544 may extend from the first end portion 506 to a first curved portion 556. A second substantially straight portion 546 may extend from the first curved portion 556 to a second curved portion 558. A third substantially straight portion 548 may extend from the second curved portion 558 to the second end portion 510. In some example embodiments, each of the substantially straight portions 544, 546, 548 may be obliquely oriented (e.g., non-parallel and non-perpendicular) with respect to each of the other substantially straight portions 544, 546, 548. For example, an angle 564 between the first substantially straight portion 544 and the second substantially straight portion 546 may be about 110 degrees to about 150 degrees and/or an angle 566 between the second substantially straight portion 546 and the third substantially straight portion 548 may be about 110 degrees to about 150 degrees. In the example embodiment shown in FIG. 12, portion 544 may have a length of about 2.9 cm, portion 546 may have a length of about 5.0 cm, portion 548 may have a length of about 2.8 cm, angle 564 may be about 128 degrees and/or angle 566 may be about 133 degrees.

Similarly, in the second jaw 504, a first substantially straight portion 550 may extend from the first end portion 508 to a first curved portion 560. A second substantially straight portion 552 may extend from the first curved portion 560 to a second curved portion 562. A third substantially straight portion 554 may extend from the second curved portion 562 to the second end portion 512. In some example embodiments, each of the substantially straight portions 550, 552, 554 may be obliquely oriented (e.g., non-parallel and non-perpendicular) with respect to each of the other substantially straight portions 550, 552, 554. For example, an angle 568 between the first substantially straight portion 550 and the second substantially straight portion 552 may be about 110 degrees to about 150 degrees and/or an angle 570 between the second substantially straight portion 552 and the third substantially straight portion 554 may be about 110 degrees to about 150 degrees. In the example embodiment shown in FIG. 13, portion 550 may have a length of about 2.9 cm, portion 552 may have a length of about 5.0 cm, portion 554 may have a length of about 2.8 cm, angle 568 may be about 128 degrees and/or angle 570 may be about 133 degrees.

In an alternative example embodiment with shorter jaws, portion 544 may have a length of less than about 2.9 cm, portion 546 may have a length of less than about 5.0 cm, portion 548 may have a length of less than about 2.8 cm, angle 564 may be about 128 degrees and/or angle 566 may be about 133 degrees. Similarly, portion 550 may have a length of less than about 2.9 cm, portion 552 may have a length of less than about 5.0 cm, portion 554 may have a length of less than about 2.8 cm, angle 568 may be about 128 degrees and/or angle 570 may be about 133 degrees.

In some example embodiments, the first jaw 502 and the second jaw 504 may be generally shaped as mirror images of one another, which may facilitate clamping the target tissue 102 between the jaws 502, 504 over any portion of their lengths. In other embodiments, the first jaw 502 and the second jaw 504 may have different dimensions.

Referring to FIGS. 3-5, 12, and 13, in some example embodiments, the respective substantially straight portions 544, 546, 548 associated with the first jaw 502 may be substantially coplanar (e.g., they may lie in substantially the same plane). Similarly, the respective substantially straight portions 550, 552, 554 associated with the second jaw 504 may be substantially coplanar. In other example embodiments, at least one of the substantially straight portions 544, 546, 548, 550, 552, 554 associated with a particular jaw 502, 504 may be substantially non-coplanar with respect to another substantially straight portion 544, 546, 548, 550, 552, 554 associated with that particular jaw 502, 504.

In some example embodiments, the first and third substantially straight portions 544, 548, 550, 554 of each jaw 502, 504 may facilitate positioning of the clamp 100 at a desired position on a patient's anatomy. For example, the first and third substantially straight portions 544, 548, 550, 554 of each jaw 502, 504 may facilitate positioning of the clamp 100 on the posterior side of the heart (e.g., on the left atrium) because they may point somewhat anteriorly. As compared to fully curved jaws, the more aggressive anterior orientation of the first and third substantially straight portions 544, 548, 550, 554 may improve positioning of the clamp 100 around the heart from an anterior surgical access location (e.g., median sternotomy).

In some example embodiments, the second substantially straight portions 546, 552 of each jaw 502, 504 may facilitate the desired engagement of the clamp 100 with a target tissue. For example, the second substantially straight portions 546, 552 of each jaw 502, 504 may facilitate the engagement of the clamp 100 with the left atrium (e.g., generally around the pulmonary veins). As compared to some fully curved jaws, the second substantially straight portions 546, 552 may engage the left atrium generally in a straight line between the right pulmonary veins and the left pulmonary veins, which may position the clamping (and ablation) location on the left atrium generally anteriorly and/or may facilitate forming an effective, transmural lesion. In addition, the second substantially straight portions 546, 552 may be less likely to slip off of the posterior aspect of the left atrium as compared to some fully curved jaws.

Referring to FIGS. 1-5, 12, and 13, in some example embodiments, the jaws 502, 504 may disposed generally distally on the head 402 and/or may be oriented generally laterally from the head 402 (e.g., generally from the first end portions 506, 508 to the second end portions 510, 512). For example, the second substantially straight portions 546, 552 of each jaw 502, 504 may be oriented approximately perpendicularly to the shaft 300. In the example embodiment illustrated in FIGS. 1-5, 12, and 13, in the closed position, the second substantially straight portions 546, 552 may be oriented at an angle of about 98 degrees with respect to the shaft 300. In an alternative example embodiment including shorter jaws, in the closed position, the second substantially straight portions 546, 552 may be oriented at an angle of about 98 degrees with respect to the shaft 300. In some other embodiments, in the closed position, the second substantially straight portions 546, 552 may be oriented at an angle of about 45 degrees to about 135 degrees with respect to the shaft 300. In other example embodiments, the jaws 502, 504 may be oriented at other angles with respect to the shaft 300, such as generally in line with the shaft 300 (e.g., extending generally directly distally).

Figure 16:
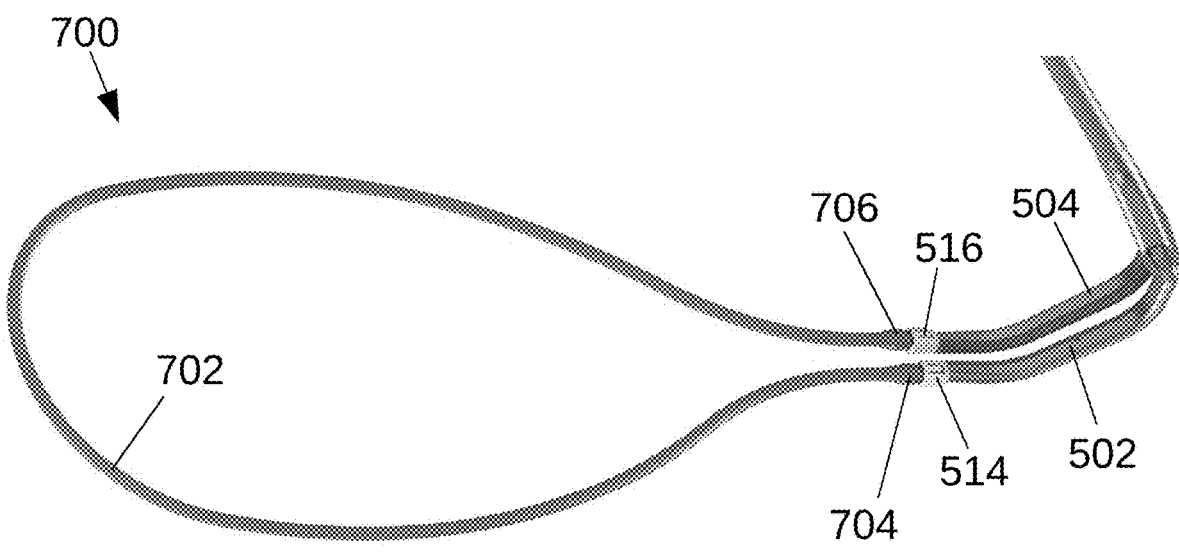
FIG. 16 is a perspective view of an example guide attached to the tips of the jaws of a clamp.
Figure 17:
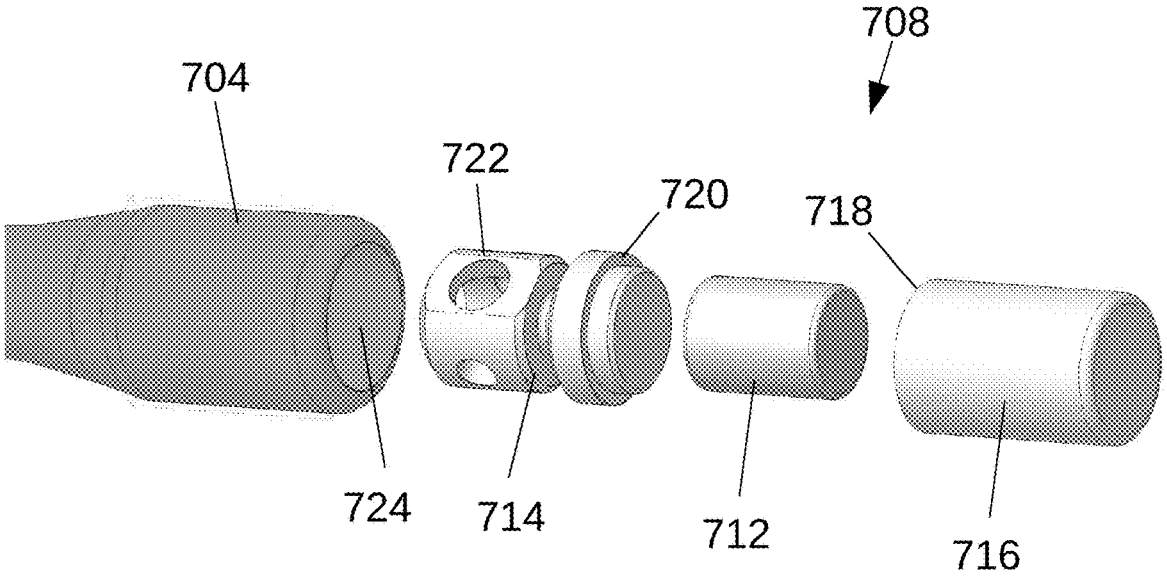
FIG. 17 is a detailed exploded perspective view of an example guide connector.

FIG. 15 is a perspective view of an example guide 700, FIG. 16 is a perspective view of an example guide 700 attached to the tips 514, 516 of the jaws 502, 504 of a clamp 100, and FIG. 17 is a detailed exploded perspective view of an example guide connector 708, all according to at least some aspects of the present disclosure. Although FIG. 17 illustrates certain components associated with the guide connector 708 associated with the first end portion 704 of the guide 700, the guide connector 710 associated with the second end portion 706 may include similar components unless otherwise specifically indicated.

Referring to FIGS. 15-17, in some example embodiments, a guide 700 may include an elongate, flexible guide body 702 extending between a first end portion 704 and a second end portion 706. In some example embodiments, the guide body 702 may be generally tubular. In some example embodiments, the guide body 702 may have a diameter of about 2.0 mm to about 10.0 mm. In some example embodiments, the guide body 702 may have a length of about 30 cm to about 180 cm. In the embodiment shown in FIGS. 15-17, the guide body 702 may have a diameter of about 5 mm and/or may have a length of about 80 cm. The guide body 702 may be constructed from thermoplastic elastic polymers, such as thermoplastic vulcanizates (TPV) (e.g., SANTOPRENE). Other potentially suitable materials for the guide body 702 include biocompatible materials having appropriate strength, flexibility, and anti-kinking properties.

In some example embodiments, one or more of the end portions 704, 706 may have a respective guide connector 708, 710 disposed thereon. In some example embodiments, the guide connectors 708, 710 may be configured to releasably couple to one another, thereby forming guide 700 into a closed loop. In some example embodiments, the guide connectors 708, 710 may be configured to releasably couple to the tips 514, 516 of the jaws 502, 504 of the clamp 100 (see FIG. 16).

Referring to FIG. 17, an example guide connector 708 may include a permanent magnet 712, which may be contained between a coupler 714 and a cover 716. For example, the cover 716 may be generally in the form of a hollow cylinder having a closed distal end and sized to receive the magnet 712 therein. A proximal surface 718 of the cover 716 may be permanently attached to a distal surface 720 of the coupler 714, such as by welding, which may securely contain the magnet 712 within the cover 716. A proximal end portion 722 of the coupler 714 may be permanently secured within a cavity 724 at the first end portion 704 of the guide body 702.

In some example guides 700 utilizing magnets 712 in their guide connectors 708, 710, the magnets may be oriented so that the guide connectors 708, 710 will magnetically couple to one another, allowing the guide 700 to form a complete, closed loop. For example, a magnet 712 in the guide connector 708 at the first end portion 704 may be oriented so that its North pole faces distally (e.g., away from the guide body 702). A magnet 712 in the guide connector 710 at the second end portion 706 may be oriented so that its South pole faces distally (e.g., away from the guide body 702). Accordingly, the distal-most ends of the magnets 712 will attract, rather than repel, each other.

In some example embodiments, the guide connectors 708, 710 may be configured to magnetically releasably couple to the tips 514, 516 of the jaws 502, 504 of the clamp 100. For example, at least a portion of the jaws 502, 504 may be constructed from a ferromagnetic material that is attracted by the magnets 712 in the guide connectors 708, 710. In some example embodiments, the guide connectors 708, 710 may be configured to mechanically releasably couple to the tips 514, 516 of the jaws 502, 504 of the clamp 100, such as by a frictional engagement, engaging a latch, snap features, etc. Further, some embodiments may utilize both mechanical and magnetic coupling. For example, referring to FIGS. 8 and 15-17, the tips 514, 516 may comprise open-ended hollow portions that may receive at least part of the covers 716 of the guide connectors 708, 710 therein. The tips 514, 516 may mechanically prevent lateral movement of the guide connectors 708, 710, and the guide connectors may be magnetically held within the tips 514, 516 by their attraction to the metal of the jaw beams 520, 522.

FIGS. 18-24 are simplified posterior perspective views of a heart 800 showing example operations using guides 700 and/or clamps 100, all according to at least some aspects of the present disclosure. While the following description focuses on the use of the guide 700 to aid in positioning the clamp 100 to form a "box lesion" around all four pulmonary veins in a single clamping and ablation operation merely as an example, one of skill in the art will recognize that various steps and methods in the following description may be utilized in connection with the guide 700 and/or the clamp 100 for other clamping and/or ablation operations.

Figures 18, 19:
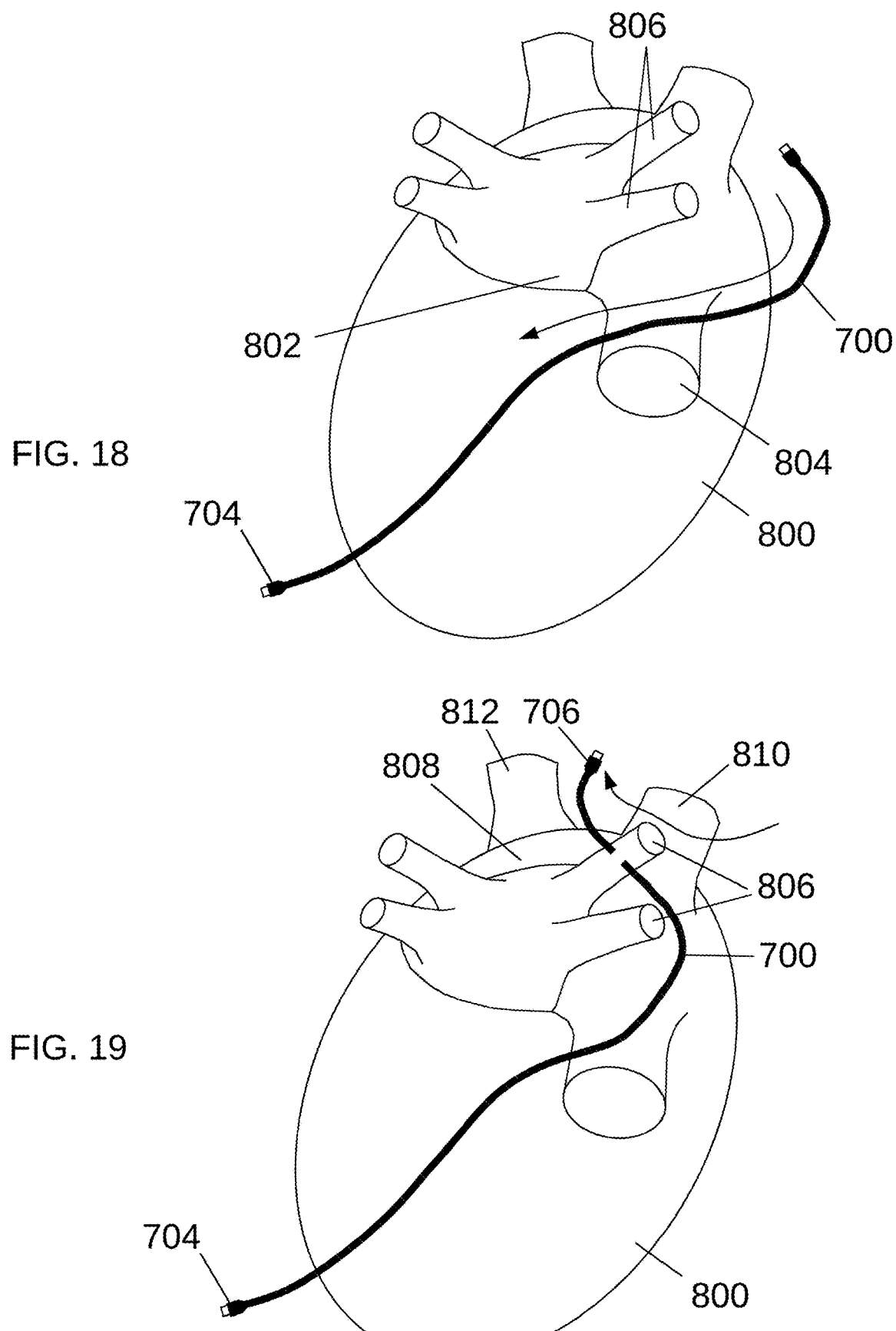
FIGS. 18-24 are simplified posterior perspective views of a heart showing example operations using guides and/or clamps.

Referring to FIG. 18, in an example method, the first end portion 704 of the guide 700 may be routed posterior to the heart 800, such as generally through the oblique sinus 802 between the inferior vena cava 804 and the right pulmonary veins 806. This may include dissecting through the pericardial reflection between the right pulmonary veins 806 and the inferior vena cava 804.

Referring to FIG. 19, in an example method, the second end portion 706 of the guide 700 may be routed posterior to the heart 800, such as partway through the transverse sinus 808 between the right pulmonary veins 806 and the superior vena cava 810. This may include dissecting through the pericardial reflection between the right pulmonary veins 806 and the superior vena cava 810. Then, the second end portion 706 may be routed generally anteriorly between the superior vena cava 810 and the aorta 812.

Figure 20:
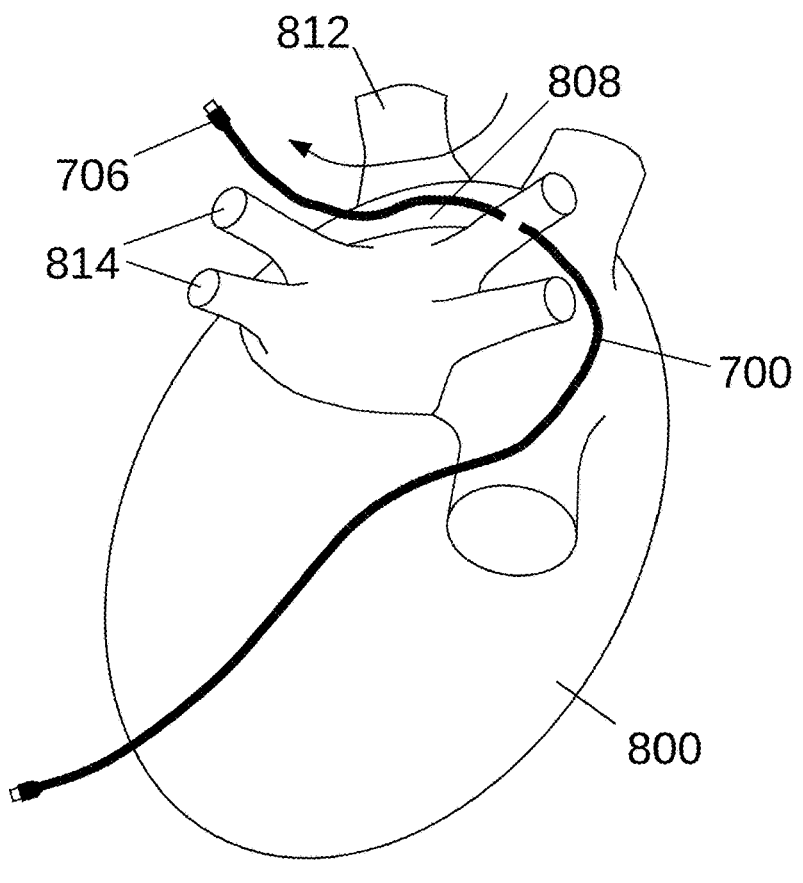

Referring to FIG. 20, in an example method, the second end portion 706 of the guide 700 may be routed through the remaining portion of the transverse sinus 808 generally between the aorta 812 and the left pulmonary veins 814.

Figure 21:
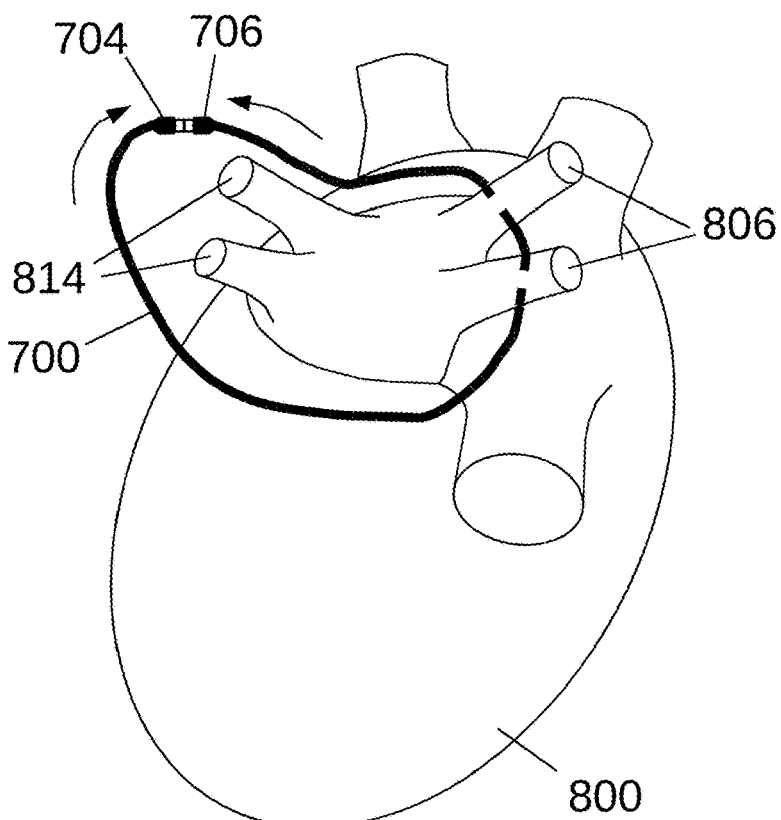

Referring to FIG. 21, in an example method, the first end portion 704 and the second end portion 706 may be releasably joined so that the guide 700 forms a complete loop generally around the pulmonary veins 806, 814. For example, the guide connectors 708, 710 (FIGS. 15 and 17) may be releasably coupled to one another (e.g., magnetically).

Figures 22, 23:
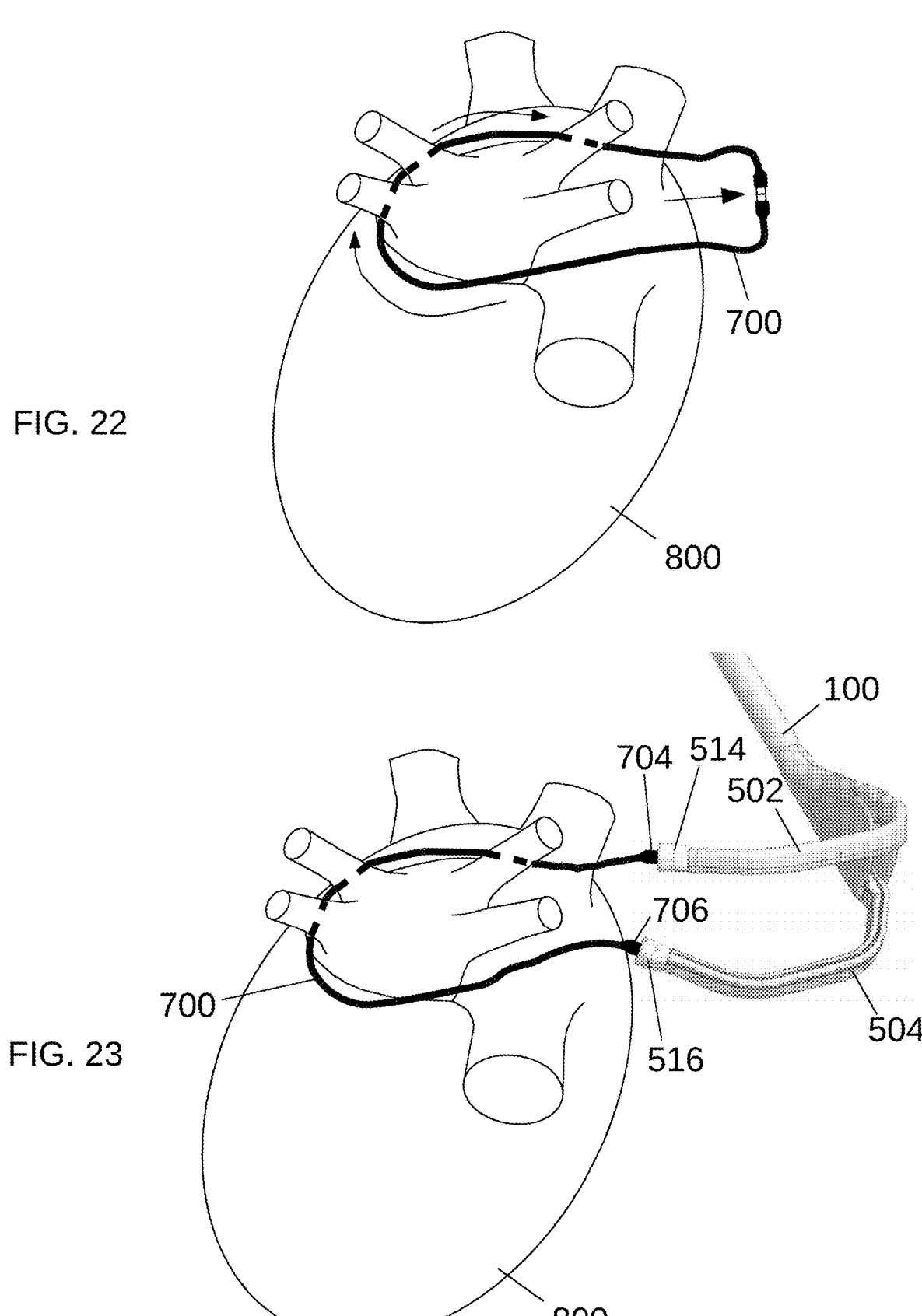

Referring to FIG. 22, in an example method, the guide 700 (e.g., as a complete loop) may be pulled generally toward the patient's right and/or may be rotated so that the guide 700 extends anteriorly from posterior to the heart 800 with the releasably coupled end portions 704, 706 generally to the patient's right.

Referring to FIG. 23, in an example method, the releasably coupled end portions 704, 706 of the guide 700 may be disconnected from one another. The first end portion 704 of the guide may be releasably connected to the tip 514 of the first jaw 502 of the clamp 100. The second end portion 706 of the guide 700 may be releasably connected to the tip 516 of the second jaw 504 of the clamp 100.

Figures 24, 25:
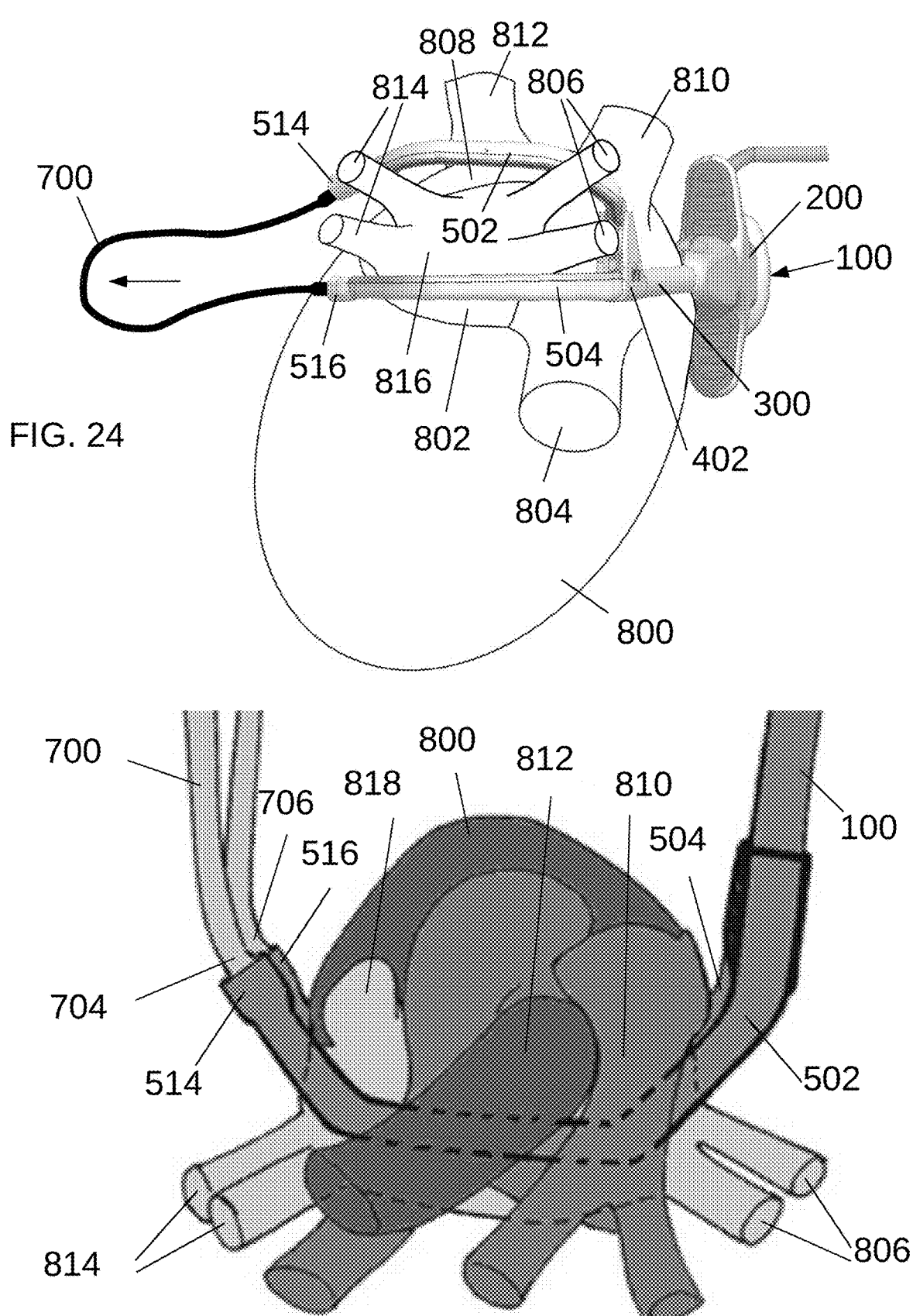
FIG. 25 is a simplified superior perspective view of a heart showing an example clamp.

Referring to FIG. 24, in an example method, the guide 700 may be pulled generally toward the patient's left, which may pull the jaws 502, 504 of the clamp 100 into a position near the pulmonary veins 806, 814 and/or the left atrium 816. The clamp 100 may be inserted generally from the anterior, right side of the patient's heart 800. The handle 200 may be generally anteriorly positioned, while the shaft 300 may extend generally posteriorly along the right side of the heart 800. The head 402 may be positioned on the right, posterior aspect of the heart 800, generally to the right of the right pulmonary veins 806. The tips 514, 516 of the jaws 502, 504 may be generally to the left of the left pulmonary veins 814. The first jaw 502 may extend generally from right to left, generally anterior and superior to the pulmonary veins 806, 814 and posterior to the superior vena cava 810 and aorta 812 (e.g., generally through the transverse sinus 808). The second jaw 504 may extend generally from right to left, generally anterior and inferior to the pulmonary veins 806, 814 and superior to the inferior vena cava 804 (e.g., generally through the oblique sinus 802).

FIG. 25 is a simplified superior perspective view of a heart 800 showing an example clamp 100, according to at least some aspects of the present disclosure. The clamp 100 may be positioned so that the left atrium 816 (FIG. 24) is clamped between the jaws 502, 504, without the jaw 502, 504 engaging the right atrium. The tips 514, 516 of the jaws 502, 504 may be positioned generally anterior to the left pulmonary veins 814. The jaws 502, 504 may be generally posterior to the left atrial appendage 818.

Figure 26:
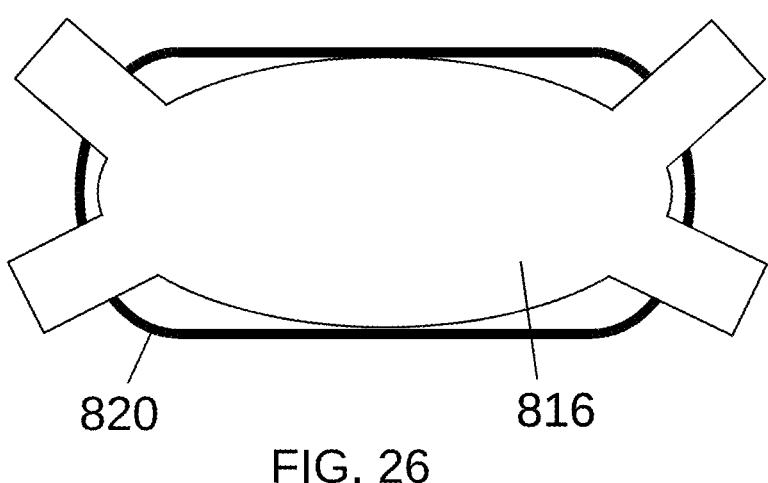
FIG. 26 is a schematic posterior view of a heart's left atrium showing an example box lesion.
Figure 27:
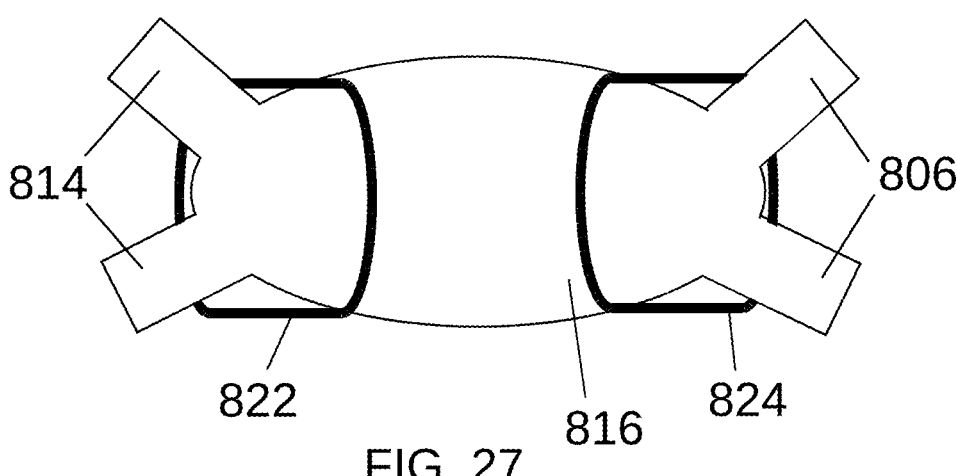
FIG. 27 is a schematic posterior view of a heart's left atrium showing example pulmonary vein isolation lesions.
Figure 28:
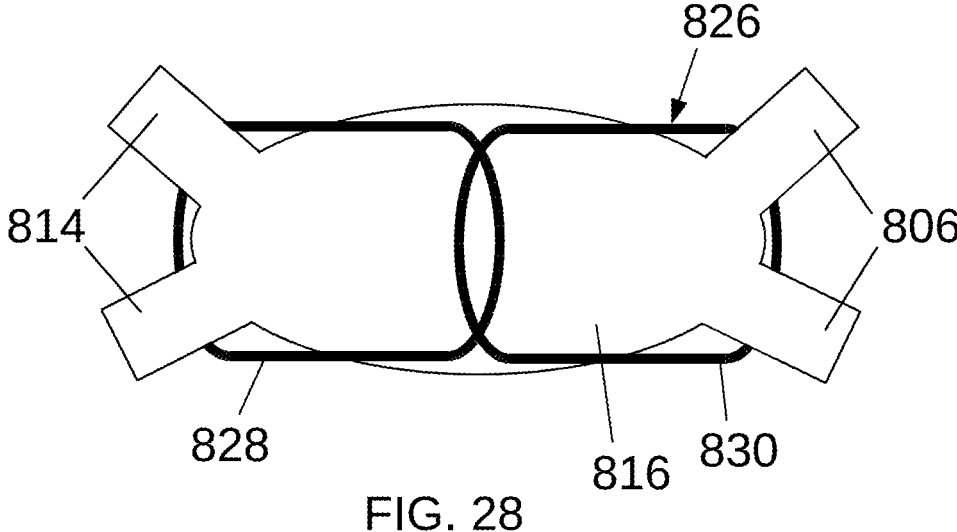
FIG. 28 is a schematic posterior view of a heart's left atrium showing an example figure-8 lesion; all in accordance with at least some aspects of the present disclosure.

FIG. 26 is a schematic posterior view of a heart's 800 left atrium 816 showing an example box lesion 820, FIG. 27 is a schematic posterior view of a heart's 800 left atrium 816 showing example pulmonary vein isolation lesions 822, 824, and FIG. 28 is a schematic posterior view of a heart's 800 left atrium 816 showing an example figure-8 lesion 826 (e.g., comprising overlapping lesions 828, 830), all according to at least some aspects of the present disclosure. Generally, the procedure described above with respect to FIGS. 18-25 may be used to create the box lesion 820 of FIG. 26, such as in a single clamping and ablating step. Alternatively, similar procedures may be used to create the pulmonary vein isolation lesions 822, 824 of FIG. 27 and/or the figure-8 lesion 826 of FIG. 28. Generally, these alternative procedures may include two or more clamping and ablating steps, such as one from a left approach and one from a right approach, in which only a portion of the left atrium 816 is clamped and ablated at one time. In some such procedures, the clamp 100 may extend partially posteriorly around the heart so that the tips 514, 516 of the jaws 502, 504 are positioned between the left pulmonary veins 814 and the right pulmonary veins 806.

Some example devices according to at least some aspects of the present disclosure may incorporate tip bias to account for the effects of tissue on the angular relationships of the jaws. For example, closing the jaws of an example clamp on tissue may cause the jaws to flex apart due to bending stress. Thus, the angular positions of the jaws when shut on tissue may differ from the angular positions of the jaws when shut empty. Some example embodiments may account for such differences by, for example, constructing the end effector such that the jaws are slightly non-parallel in the closed position when the jaws are empty. For example, the tips of the jaws may be biased inward from parallel by about 0.020 inches in the closed position when empty, which may result in the jaws being substantially parallel in the closed position when tissue is between the jaws. More generally, in some example embodiments, the design of the end effector and the jaws may be such that the jaws are substantially parallel when actuated on tissue.

Following from the above description and invention summaries, it should be apparent to those of ordinary skill in the art that, while the methods and apparatuses herein described constitute example embodiments according to the present disclosure, it is to be understood that the scope of the disclosure contained herein is not limited to the above precise embodiments and that changes may be made without departing from the scope as defined by the following claims. Likewise, it is to be understood that it is not necessary to meet any or all of the identified advantages or objects disclosed herein in order to fall within the scope of the claims, since inherent and/or unforeseen advantages may exist even though they may not have been explicitly discussed herein.

What is claimed is:

1. A surgical device, comprising:

a shaft;

an end effector disposed at a distal end of the shaft, the end effector comprising a head, the head comprising an articulating mechanism, the articulating mechanism being operable to move a first jaw between an open position in which the first jaw and a second jaw are separated and substantially non-parallel and a closed position in which the first jaw and the second jaw are substantially adjacent and substantially parallel; and an elongate, flexible guide body including a first end portion and a second end portion;

wherein the first end portion includes a first ferromagnetic connector, and the second end portion includes a second ferromagnetic connector, wherein each of the first jaw and the second jaw comprises a first substantially straight portion proximate the head, a second substantially straight portion, a third substantially straight portion distant from the head, a first curved portion between the first substantially straight portion and the second substantially straight portion, and a second curved portion between the second substantially straight portion and the third substantially straight portion;

wherein each of the first jaw and the second jaw comprises at least one electrode;

wherein the first jaw includes a first jaw ferromagnetic connector, and the second jaw includes a second jaw ferromagnetic connector; and wherein the first guide connector is configured to releasably engage the first jaw ferromagnetic connector and the second guide connector is configured to releasably engage the second jaw ferromagnetic connector to form a continuous, closed loop in both the open position and the closed position.

2. The surgical device of claim 1, wherein the articulating mechanism is operable to rotate and translate the first jaw between the open position, an intermediate position in which the first jaw and the second jaw are separated and substantially parallel, and the closed position.

3. The surgical device of claim 1, wherein the first substantially straight portion, the second substantially straight portion, and the third substantially straight portion of the first jaw are obliquely oriented with respect to each other.

4. The surgical device of claim 1, wherein the first substantially straight portion, the second substantially straight portion, and the third substantially straight portion of the second jaw are obliquely oriented with respect to each other.

5. The surgical device of claim 1, wherein the first substantially straight portion, the second substantially straight portion, and the third substantially straight portion of the first jaw are substantially coplanar.

6. The surgical device of claim 1, wherein the first substantially straight portion, the second substantially straight portion, and the third substantially straight portion of the second jaw are substantially coplanar.

7. The surgical device of claim 1, wherein the second substantially straight portion of the first jaw is longer than at least one of the first substantially straight portion of the first jaw and the second substantially straight portion of the first jaw.

8. The surgical device of claim 1, wherein the first jaw and the second jaw are disposed generally distally on the head; and wherein the first jaw and the second jaw are oriented generally laterally from the head.

9. The surgical device of claim 1, wherein, in the closed position, the first substantially straight portion of the first jaw extends generally diagonally distally and laterally away from the head.

10. The surgical device of claim 1, wherein the third substantially straight portion of the first jaw extends generally diagonally proximally and laterally away from the second curved portion.

11. The surgical device of claim 1, wherein the second jaw is rigidly disposed with respect to the shaft.

12. The surgical device of claim 1, further comprising a handle disposed proximally on the shaft, the handle comprising an actuator operatively connected to the articulating mechanism.

13. The surgical device of claim 1, wherein the articulating mechanism comprises a first jaw mount coupled to the first jaw, the first jaw mount being movable along a path, wherein movement of the first jaw mount along the path causes rotation and translation of the first jaw mount and the first jaw, thereby moving the first jaw between the open position and the closed position; and a pivotably mounted crank, the crank operably coupling an actuator linkage to the first jaw mount so that moving the actuator linkage rotates the crank, wherein rotation of the crank moves the first jaw mount along the path.

14. A guide for a surgical device, the guide comprising:

an elongate, flexible guide body including a first end portion and a second end portion;

a first guide connector disposed on the first end portion; and a second guide connector disposed on the second end portion;

wherein the first guide connector is selectively releasably connectable to the second guide connector and at least one of a first tip of a first jaw of a surgical device and a second tip of a second jaw of the surgical device;

wherein the second guide connector is selectively releasably connectable to the first guide connector and at least one of the first tip and the second tip; and wherein, when the first guide connector is connected to the second guide connector, the guide forms a continuous, closed loop;

wherein the first guide connector comprises a first permanent magnet;

wherein the second guide connector comprises a second permanent magnet; and wherein the first permanent magnet and the second permanent magnet are oriented so that opposite magnetic poles face away from the guide body, thereby allowing the first guide connector and the second guide connector to magnetically couple to one another to form the guide into the continuous, closed loop.

15. A surgical apparatus, comprising:

a surgical device comprising a handle, a shaft extending distally from the handle, and an end effector disposed proximate a distal end of the shaft, the end effector comprising the first jaw and the second jaw; and the guide of claim 14.

16. A method of using a surgical device, the method comprising:

positioning an elongate, flexible guide using opposing end couplings to form a continuous, closed loop around right pulmonary veins and left pulmonary veins of a heart;

disengaging the opposing end couplings from one another to discontinue the continuous, closed loop while still extending around at least one of the right pulmonary veins and the left pulmonary veins;

coupling a first of the opposing end couplings to a tip of a first jaw of a clamp;

coupling a second of the opposing end couplings a tip of
    a second jaw of the clamp;
positioning the first jaw and the second jaw proximate a
    left atrium of the heart by pulling the guide; and
clamping a portion of the left atrium between the first jaw
    and the second jaw.

* * * * *